(12) United States Patent
Frazer

(10) Patent No.: US 7,901,905 B2
(45) Date of Patent: Mar. 8, 2011

(54) GENE EXPRESSION SYSTEM BASED ON CODON TRANSLATION EFFICIENCY

(75) Inventor: Ian Hector Frazer, Queensland (AU)

(73) Assignee: The University of Queensland, St. Lucia, Queensland (AU)

( * ) Notice: Subject to any disclaimer, the term of this patent is extended or adjusted under 35 U.S.C. 154(b) by 525 days.

(21) Appl. No.: 11/077,939

(22) Filed: Mar. 11, 2005

(65) Prior Publication Data

US 2005/0196865 A1 Sep. 8, 2005

Related U.S. Application Data

(63) Continuation of application No. PCT/AU03/01200, filed on Sep. 15, 2003.

(60) Provisional application No. 60/410,410, filed on Sep. 13, 2002.

(51) Int. Cl.
*C12P 21/02* (2006.01)
(52) U.S. Cl. ...................... 435/69.1; 435/235.1; 435/462; 435/358
(58) Field of Classification Search .................. None
See application file for complete search history.

(56) References Cited

U.S. PATENT DOCUMENTS 5,736,318 A * 4/1998 Munger et al. .................... 435/5
6,602,705 B1 * 8/2003 Barnett et al. ............. 435/320.1

FOREIGN PATENT DOCUMENTS

| WO | WO 00/42190 A1 | 7/2000 |
| WO | WO 00/42215 A1 | 7/2000 |
| WO | WO 00/44926 A1 | 8/2000 |

OTHER PUBLICATIONS

Wells et al., Transgenic Research, vol. 8, 1999, pp. 371-381.*
Ikemura, Toshimichi, "Codon Usage and tRNA Content in Unicellular and Multicellular Organisms," *Mol. Biol. Evol.* 2(1):13-34 (1985).
Zhou, Jian, et al., "Papillomavirus Capsid Protein Expression Level Depends on the Match between Codon Usuage and tRNA Availability," *Journal of Virology* 73(6):4972-4982 (Jun. 1999).
Moustafa, Mohamed E., et al., "Overproduction of selenocysteine tRNA in Chinese hamster ovary cells following transfection of the mouse tRNA$^{[Ser]Sec}$ gene," *RNA* 4:1436-1443 (1998).

Duret, "tRNA gene number and condon usage in the C. elegans genome are co-adapted for opitmal translation of highly expressed genes", Trends in Genetics, Elsevier, Amsterdam, NL, vol. 16, No. 7, pp. 287-289 (2000).
Moriyama et al., "Condon usage bias and tRNA abundance in Drosophila", Journal of Molecular Evolution, vol. 45, No. 5, pp. 514-523 (1997).
Zhao et al., "Effects of additional sequences directly downstream from the AUG on the expression of GFP gene", Biochimica et Biophysica Acta, vol. 1630, No. 2-3, pp. 84-95 (2003).
Zhao et al., "Gene Condon Composition Determines Differentiation-Dependent Express of a Viral Capsid Gene in Keratinocytes In Vitro and In Vivo", Molecular and Cellular Biology, vol. 25, No. 19, pp. 8643-8655 (2005).
Gu et al., "tRNASer(GCA) differentially regulates expression of wild-type and codon-modified papillomavirus L1 genes", Nucleic Acids Research, vol. 32, No. 15, pp. 4448-4461 (2004).
Miyagawa S. et al., (2001, Journal of Biochemistry, 129(5): 795-801).
Grillari J. et al. (2001, Journal of Biotechnology, 87(1): 59-65).
Koresawa Y. et al. (2000, Journal of Biochemistry, 127(3): 367-372).
Werstuck G. et al., (1998, Science, 282(5387): 296-298).
Kakinuma A. et al., (1996, Endocrinology, 137(7): 2664-2669).
Tanguay R.L. et al., (1996, Molecular and Cellular Biology, 16(1): 146-156).
Cumin F. et al., (1993, European Journal of Biochemistry, 212(2): 347-354).
International Preliminary Examination Report from PCT/AU2003/001200 dated Jan. 12, 2005.
Kim et al., "Codon optimization for high-level expression of human erythropoietin (EPO) in mammalian cells," Gene, 199 (1997), pp. 293-301.

* cited by examiner

*Primary Examiner* — James S Ketter
(74) *Attorney, Agent, or Firm* — Panitch Schwarze Belisario & Nadel LLP

(57) ABSTRACT

The present invention discloses a method for modulating the production of a protein from a polynucleotide in a CHO cell by replacing at least one codon of the polynucleotide with a synonymous codon that has a higher or lower translation efficiency in the CHO cell than the codon it replaces, or by introducing into the CHO cell a polynucleotide that codes for an iso-tRNA which limits the rate of production of the polypeptide and which corresponds to a codon of the first polynucleotide. The present invention also discloses the use of a protein-encoding polynucleotide whose codon composition has been modified for enhanced production of the protein in CHO cells.

6 Claims, 9 Drawing Sheets

```
                  M  A  P  V  A  V  W  A  A  L  A  V  G  L  E  L  W  A  A  A
Enbrel    1       atggcgcccgtcgccgtctgggccgcgctggccgtcggactggagctctgggctgcggcg 60
modified  1       .............................c...........c..a............... 3

H  A  L  P  A  Q  V  A  F  T  P  Y  A  P  E  P  G  S  T  C
Enbrel    61      cacgccttgcccgcccaggtggcatttacaccctacgccccggagcccgggagcacatgc 120
modified  3       ............................................a.....a......... 5

R  L  R  E  Y  Y  D  Q  T  A  Q  M  C  C  S  K  C  S  P  G
Enbrel    121     cggctcagagaatactatgaccagacagctcagatgtgctgcagcaaatgctcgccgggc 180
modified  5       ...............................................g...........a 7

Q  H  A  K  V  F  C  T  K  T  S  D  T  V  C  D  S  C  E  D
Enbrel    181     caacatgcaaaagtcttctgtaccaagacctcggacaccgtgtgtgactcctgtgaggac 240
modified  7       .....c.....g.....t.....a.....a.............................. 12

S  T  Y  T  Q  L  W  N  W  V  P  E  C  L  S  C  G  S  R  C
Enbrel    241     agcacatacacccagctctggaactgggttcccgagtgcttgagctgtggctcccgctgt 300
modified  12      ............................................................ 12

S  S  D  Q  V  E  T  Q  A  C  T  R  E  Q  N  R  I  C  T  C
Enbrel    301     agctctgaccaggtggaaactcaagcctgcactcgggaacagaaccgcatctgcacctgc 360
modified  12      ............................................................ 12

R  P  G  W  Y  C  A  L  S  K  Q  E  G  C  R  L  C  A  P  L
Enbrel    361     aggcccggctggtactgcgcgctgagcaagcaggaggggtgccggctgtgcgcgccgctg 420
modified  12      ............................................................ 12

R  K  C  R  P  G  F  G  V  A  R  P  G  T  E  T  S  D  V  V
Enbrel    421     cgcaagtgccgcccgggcttcggcgtggccagaccaggaactgaaacatcagacgtggtg 480
modified  12      ............................................................ 12

C  K  P  C  A  P  G  T  F  S  N  T  T  S  S  T  D  I  C  R
Enbrel    481     tgcaagccctgtgccccggggacgttctccaacacgacttcatccacggatatttgcagg 540
modified  12      ............................................................ 12

P  H  Q  I  C  N  V  V  A  I  P  G  N  A  S  M  D  A  V  C
Enbrel    541     ccccaccagatctgtaacgtggtggccatccctgggaatgcaagcatggatgcagtctgc 600
modified  12      ............................................................ 12
```

FIGURE 1-1

```
                  T  S  T  S  P  T  R  S  M  A  P  G  A  V  H  L  P  Q  P  V
Enbrel    601   acgtccacgtcccccacccggagtatggccccaggggcagtacacttaccccagccagtg 660
modified  12    ............................................................ 12

S  T  R  S  Q  H  T  Q  P  T  P  E  P  S  T  A  P  S  T  S
Enbrel    661   tccacacgatcccaacacacgcagccaactccagaacccagcactgctccaagcacctcc 720
modified  12    ............................................................ 12

F  L  L  P  M  G  P  S  P  P  A  E  G  S  T  G  D  E  P  K
Enbrel    721   ttcctgctcccaatgggccccagcccccccagctgaagggagcactggcgacgagcccaaa 780
modified  12    ............................................................ 12

S  C  D  K  T  H  T  C  P  P  C  P  A  P  E  L  L  G  G  P
Enbrel    781   tcttgtgacaaaactcacacatgcccaccgtgcccagcacctgaactcctggggggaccg 840
modified  12    ............................................................ 12

S  V  F  L  F  P  P  K  P  K  D  T  L  M  I  S  R  T  P  E
Enbrel    841   tcagtcttcctcttccccccaaaacccaaggacaccctcatgatctcccggacccctgag 900
modified  12    ............................................................ 12

V  T  C  V  V  V  D  V  S  H  E  D  P  E  V  K  F  N  W  Y
Enbrel    901   gtcacatgcgtggtggtggacgtgagccacgaagaccctgaggtcaagttcaactggtac 960
modified  12    ............................................................ 12

V  D  G  V  E  V  H  N  A  K  T  K  P  R  E  E  Q  Y  N  S
Enbrel    961   gtggacggcgtggaggtgcataatgccaagacaaagccgcgggaggagcagtacaacagc 1020
modified  12    ............................................................ 12

T  Y  R  V  V  S  V  L  T  V  L  H  Q  D  W  L  N  G  K  E
Enbrel    1021  acgtaccgtgtggtcagcgtcctcaccgtcctgcaccaggactggctgaatggcaaggag 1080
modified  12    ............................................................ 12

Y  K  C  K  V  S  N  K  A  L  P  A  P  I  E  K  T  I  S  K
Enbrel    1081  tacaagtgcaaggtctccaacaaagccctcccagcccccatcgagaaaaccatctccaaa 1140
modified  12    ............................................................ 12

A  K  G  Q  P  R  E  P  Q  V  Y  T  L  P  P  S  R  E  E  M
Enbrel    1141  gccaaagggcagccccgagaaccacaggtgtacaccctgcccccatcccgggaggagatg 1200
modified  12    ............................................................ 12
```

FIGURE 1-2

```
                   T  K  N  Q  V  S  L  T  C  L  V  K  G  F  Y  P  S  D  I  A
Enbrel    1201 accaagaaccaggtcagcctgacctgcctggtcaaaggcttctatcccagcgacatcgcc 1260
modified  12   ............................................................ 12

V  E  W  E  S  N  G  Q  P  E  N  N  Y  K  T  T  P  P  V  L
Enbrel    1261 gtggagtgggagagcaatgggcagccggagaacaactacaagaccacgcctcccgtgctg 1320
modified  12   ............................................................ 12

D  S  D  G  S  F  F  L  Y  S  K  L  T  V  D  K  S  R  W  Q
Enbrel    1321 gactccgacggctccttcttcctctatagcaagctcaccgtggacaagagcaggtggcag 1380
modified  12   ............................................................ 12

Q  G  N  V  F  S  C  S  V  M  H  E  A  L  H  N  H  Y  T  Q
Enbrel    1381 caggggaacgtcttctcatgctccgtgatgcatgaggctctgcacaaccactacacgcag 1440
modified  12   ............................................................ 12

K  S  L  S  L  S  P  G  K  *
Enbrel    1441 aagagcctctccctgtctccgggtaaatga 1470
modified  12   .............................. 12
```

FIGURE 1-3

```
              M H G D T P T L H E Y M L D L Q P E T L
HPV16E7   1   atgcatggagatacacctacattgcatgaatatatgttagatttgcaaccagagacaact   60
modified  1   .....c............c...c.c..c..........c.c...c.c.....c..a.....a  12

D L Y C Y E Q L N D S S E E E D E I D G
HPV16E7   61  gatctctactgttatgagcaattaaatgacagctcagaggaggaggatgaaatagatggt   120
modified  12  ...........c.....a...c.c..c...t.....t..a..a...a.............a  23

P A G Q A E P D R A H Y N I V T F C K
HPV16E7   121 ccagctggacaagcagaaccggacagagcccattacaatattgtaacctttttgttgcaag   180
modified  23  .....a..............c..t.....a..c.....c.........a.....c......  31

C D S T L R L C V Q S T H V D I R T L E
HPV16E7   181 tgtgactctacgcttcggttgtgcgtacaaagcacacacgtagacattcgtactttggaa   240
modified  31  ..c..t.........c....c.c........................t........ac.c...  40

D L L M G T L G I V C P I C S Q K P *
HPV16E7   241 gacctgttaatgggcacactaggaattgtgtgcccatctgttctcagaaaccataa      297
modified  40  ..t..cc.c.....a......c....................c........g..c...     49
```

FIGURE 2

```
                        M  A  T  G  S  R  T  S  L  L  L  A  F  G  L  L  C  L  P  W
Human GH    1  atggctacaggctcccggacgtccctgctcctggcttttggcctgctctgcctgccctgg  60
modified    1  .....a......a..t.........t..c.....c..a.....a...c........c......  10

L  Q  E  G  S  A  S  P  T  I  P  L  S  R  P  F  D  N  A  M
Human GH   61  cttcaagagggcagtgccttcccaaccattcccttatccaggccttttgacaacgctatg  120
modified   10  ..c.....a..a..c..a..t..c..a......c.c..t..a..c.....t.....a...  25

L  R  A  H  R  L  H  Q  L  A  F  D  T  Y  Q  E  F  E  E  A
Human GH  121  ctccgcgcccatcgtctgcaccagctggcctttgacacctaccaggagtttgaagaagcc  180
modified   25  .....g..a..c.....c.........c...a.........a..........a..........a  34

Y  I  P  K  E  Q  K  Y  S  F  L  Q  N  P  Q  T  S  L  C  F
Human GH  181  tatatcccaaaggaacagaagtattcattcctgcagaaccccagacctccctctgtttc  240
modified   34  ........c....................t..t...............................  37

S  E  S  I  P  T  P  S  N  R  E  E  T  Q  Q  K  S  N  L  E
Human GH  241  tcagagtctattccgacaccctccaacagggaggaaacacaacagaaatccaacctagag  300
modified   37  ............................................................  37

L  L  R  I  S  L  L  L  I  Q  S  W  L  E  P  V  Q  F  L  R
Human GH  301  ctgctccgcatctccctgctgctcatccagtcgtggctggagcccgtgcagttcctcagg  360
modified   37  ............................................................  37

S  V  F  A  N  S  L  V  Y  G  A  S  D  S  N  V  Y  D  L  L
Human GH  361  agtgtcttcgccaacagcctggtgtacggcgcctctgacagcaacgtctatgacctccta  420
modified   37  ............................................................  37

K  D  L  E  E  G  I  Q  T  L  M  G  R  L  E  D  G  S  P  R
Human GH  421  aaggacctagaggaaggcatccaaacgctgatggggaggctggaagatggcagcccccgg  480
modified   37  ............................................................  37

T  G  Q  I  F  K  Q  T  Y  S  K  F  D  T  N  S  H  N  D  D
Human GH  481  actgggcagatcttcaagcagacctacagcaagttcgacacaaactcacacaacgatgac  540
modified   37  ............................................................  37

A  L  L  K  N  Y  G  L  L  Y  C  F  R  K  D  M  D  K  V  E
Human GH  541  gcactactcaagaactacggctgctctactgcttcaggaaggacatggacaaggtcgag  600
modified   37  ............................................................  37

T  F  L  R  I  V  Q  C  R  S  V  E  G  S  C  G  F  *
Human GH  601  acattcctgcgcatcgtgcagtgccgctctgtggagggcagctgtggcttctag  654
modified   37  ......................................................  37
```

FIGURE 3

```
Genomic hGH  caaggatccc aaggcccaac tccccgaacc actcagggtc ctgtggacag ctcacctagc    60
Modified hGH  .......... .......... .......... .......... .......... ..........

M   A   T                                                    3
Genomic hGH  tgca atg gct aca g gtaagcgccc ctaaaatccc tttggcacaa tgtgtcctga    114
Modified hGH  .... ... ... ... . .......... .......... .......... ..........

Genomic hGH  ggggagaggc agcgacctgt agatgggacg ggggcactaa ccctcaggtt tggggcttct   174
Modified hGH  .......... .......... .......... .......... .......... ..........

Genomic hGH  gaatgtgagt atcgccatgt aagcccagta tttggccaat ctcagaaagc tcctggtccc   234
Modified hGH  .......... .......... .......... .......... .......... ..........

Genomic hGH  tggagggatg gagagagaaa aacaaacagc tcctggagca gggagagtgc tggcctcttg   294
Modified hGH  .......... .......... .......... .......... .......... ..........

(                                                       G   S   R   T   S
Genomic hGH  ctctccggct ccctctgttg ccctctggtt tctccccag gc  tcc cgg acg tcc       347
Modified hGH  .......... .......... .......... ..........  a  ..t ... ... ..t      3

L   L   L   A   F   G   L   L   C   L   P   W   L   Q   E   G
Genomic hGH  ctg ctc ctg gct ttt ggc ctg ctc tgc ctg ccc tgg ctt caa gag ggc       395
Modified hGH  ..c ... ..c ..a ... ..a ..c ... ... ..c ... ... ..c ... ..a ..a       12

S   A   F   P   T   I   P   L   S   R   P   F   D   N   A   M
Genomic hGH  agt gcc ttc cca acc att ccc tta tcc agg cct ttt gac aac gct atg       443
Modified hGH  ..c ..a ..t ..c ..a ... ... c.c ..t ..a ..c ... ..t ... ..a ...       24

L   R   A   H   R   L   H   Q   L   A   F   D   T   Y   Q   E
Genomic hGH  ctc cgc gcc cat cgt ctg cac cag ctg gcc ttt gac acc tac cag gag       491
Modified hGH  ... ..g ..a ..c ... ..c ... ... ... ... ... ... ..a ... ... ..a       30

F
Genomic hGH  ttt gtaagctctt ggggaatggg tgcgcatcag gggtggcagg aagggggtgac          544
Modified hGH  ... .......... .......... .......... .......... ..........           30

Genomic hGH  tttcccccgc tgggaaataa gaggaggaga ctaaggagct cagggttttt cccgaagcga    604
Modified hGH  .......... .......... .......... .......... .......... ..........

Genomic hGH  aaatgcaggc agatgagcac acgctgagtg aggttcccag aaaagtaaca atgggagctg    664
Modified hGH  .......... .......... .......... .......... .......... ..........    30

E   E   A   Y   I
Genomic hGH  gtctccagcg tagaccttgg tgggcggtcc ttctcctag gaa gaa gcc tat atc       718
Modified hGH  .......... .......... .......... ..........  ...  ... ... ... ...    30

P   K   E   Q   K   Y   S   F   L   Q   N   P   Q   T   S   L
Genomic hGH  cca aag gaa cag aag tat tca ttc ctg cag aac ccc cag acc tcc ctc       766
Modified hGH  ... ... ... ... ... ... ... ... ... ... ... ... ... ... ... ...       30

C   F   S   E   S   I   P   T   P   S   N   R   E   E   T   Q
Genomic hGH  tgt ttc tca gag tct att ccg aca ccc tcc aac agg gag gaa aca caa       814
Modified hGH  .......... .......... .......... .......... .......... ..........    30

Q   K   S
Genomic hGH  cag aaa tcc gtgagtggat gccttctccc caggcgggga tggggagac              863
Modified hGH  ... ... ... .......... .......... .......... ..........
```

FIGURE 4-1

```
                                                                            N   L
Genomic hGH  ctgtagtcag agcccccggg cagcacagcc aatgcccgtc cttcccctgc ag aac cta   921
Modified hGH ........................................................... ..  ...  ...   30

E   L   L   R   I   S   L   L   L   I   Q   S   W   L   E   P
Genomic hGH  gag ctg ctc cgc atc tcc ctg ctg ctc atc cag tcg tgg ctg gag ccc   969
Modified hGH ... ... ... ... ... ... ... ... ... ... ... ... ... ... ... ...   30

V   Q   F   L   R   S   V   F   A   N   S   L   V   Y   G   A
Genomic hGH  gtg cag ttc ctc agg agt gtc ttc gcc aac agc ctg gtg tac ggc gcc  1017
Modified hGH ... ... ... ... ... ... ... ... ... ... ... ... ... ... ... ...   30

S   D   S   N   V   Y   D   L   L   K   D   L   E   E   G   I
Genomic hGH  tct gac agc aac gtc tat gac ctc cta aag gac cta gag gaa ggc atc  1065
Modified hGH ... ... ... ... ... ... ... ... ... ... ... ... ... ... ... ...   30

Q   T   L   M   G
Genomic hGH  caa acg ctg atg ggg gtgagggtgg cgccagggggt ccccaatcct ggagccccac  1120
Modified hGH ... ... ... ... ... .......... .......... .......... ..........   30

Genomic hGH  tgactttgag agctgtgtta gagaaacact gctgccctct ttttagcagt caggccctga  1180
Modified hGH .......... .......... .......... .......... .......... ..........   30

Genomic hGH  cccaagagaa ctcaccttat tcttcatttc ccctcgtgaa tcctccaggc ctttctctac  1240
Modified hGH .......... .......... .......... .......... .......... ..........   30

Genomic hGH  accctgaagg ggagggagga aaatgaatga atgagaaagg gagggaacag tacccaagcg  1300
Modified hGH .......... .......... .......... .......... .......... ..........   30

R   L   E   D   G   S   P
Genomic hGH  cttggcctct ccttctcttc cttcactttg cag agg ctg gaa gat ggc agc ccc  1354
Modified hGH .......... .......... .......... ... ... ... ... ... ... ... ...   30

R   T   G   Q   I   F   K   Q   T   Y   S   K   F   D   T   N
Genomic hGH  cgg act ggg cag atc ttc aag cag acc tac agc aag ttc gac aca aac  1402
Modified hGH ... ... ... ... ... ... ... ... ... ... ... ... ... ... ... ...   30

S   H   N   D   D   A   L   L   K   N   Y   G   L   L   Y   C
Genomic hGH  tca cac aac gat gac gca cta ctc aag aac tac ggg ctg ctc tac tgc  1450
Modified hGH ... ... ... ... ... ... ... ... ... ... ... ... ... ... ... ...   30

F   R   K   D   M   D   K   V   E   T   F   L   R   I   V   Q
Genomic hGH  ttc agg aag gac atg gac aag gtc gag aca ttc ctg cgc atc gtg cag  1498
Modified hGH ... ... ... ... ... ... ... ... ... ... ... ... ... ... ... ...   30

C   R   S   V   E   G   S   C   G   F
Genomic hGH  tgc cgc tct gtg gag ggc agc tgt ggc ttc tagctgcccg ggtggcatcc  1548
Modified hGH ... ... ... ... ... ... ... ... ... ... .......... ..........   30

Genomic hGH  ctgtgacccc tccccagtgc ctctcctggc cctggaagtt gccactccag tgcccaccag  1608
Modified hGH .......... .......... .......... .......... .......... ..........   30

Genomic hGH  ccttgtccta ataaaattaa gttgcatcat tttgtctgac taggtgtcct tctataatat  1668
Modified hGH .......... .......... .......... .......... .......... ..........   30

Genomic hGH  tatggggtgg a                                                      1679
Modified hGH .......... .                                                        30
```

FIGURE 4-2

SEQUENCE LISTING

```
<160> NUMBER OF SEQ ID NOS: 28

<210> SEQ ID NO 1
<211> LENGTH: 1470
<212> TYPE: DNA
<213> ORGANISM: Artificial Sequence
<220> FEATURE:
<223> OTHER INFORMATION: DNA encoding Enbrel, a recombinant fusion
      protein consisting of two soluble TNF receptors joined by the Fc
      fragment of a human IgG1 molecule
<220> FEATURE:
<221> NAME/KEY: CDS
<222> LOCATION: (1)..(1467)

<400> SEQUENCE: 1 atg gcg ccc gtc gcc gtc tgg gcc gcg ctg gcc gtc gga ctg gag ctc      48
Met Ala Pro Val Ala Val Trp Ala Ala Leu Ala Val Gly Leu Glu Leu
1               5                   10                  15 tgg gct gcg gcg cac gcc ttg ccc gcc cag gtg gca ttt aca ccc tac      96
Trp Ala Ala Ala His Ala Leu Pro Ala Gln Val Ala Phe Thr Pro Tyr
```

```
                 20                      25                      30
gcc ccg gag ccc ggg agc aca tgc cgg ctc aga gaa tac tat gac cag      144
Ala Pro Glu Pro Gly Ser Thr Cys Arg Leu Arg Glu Tyr Tyr Asp Gln
         35                      40                      45 aca gct cag atg tgc tgc agc aaa tgc tcg ccg ggc caa cat gca aaa      192
Thr Ala Gln Met Cys Cys Ser Lys Cys Ser Pro Gly Gln His Ala Lys
 50                      55                      60 gtc ttc tgt acc aag acc tcg gac acc gtg tgt gac tcc tgt gag gac      240
Val Phe Cys Thr Lys Thr Ser Asp Thr Val Cys Asp Ser Cys Glu Asp
 65                      70                      75                      80 agc aca tac acc cag ctc tgg aac tgg gtt ccc gag tgc ttg agc tgt      288
Ser Thr Tyr Thr Gln Leu Trp Asn Trp Val Pro Glu Cys Leu Ser Cys
                 85                      90                      95 ggc tcc cgc tgt agc tct gac cag gtg gaa act caa gcc tgc act cgg      336
Gly Ser Arg Cys Ser Ser Asp Gln Val Glu Thr Gln Ala Cys Thr Arg
             100                     105                     110 gaa cag aac cgc atc tgc acc tgc agg ccc ggc tgg tac tgc gcg ctg      384
Glu Gln Asn Arg Ile Cys Thr Cys Arg Pro Gly Trp Tyr Cys Ala Leu
             115                     120                     125 agc aag cag gag ggg tgc cgg ctg tgc gcg ccg ctg cgc aag tgc cgc      432
Ser Lys Gln Glu Gly Cys Arg Leu Cys Ala Pro Leu Arg Lys Cys Arg
 130                     135                     140 ccg ggc ttc ggc gtg gcc aga cca gga act gaa aca tca gac gtg gtg      480
Pro Gly Phe Gly Val Ala Arg Pro Gly Thr Glu Thr Ser Asp Val Val
145                     150                     155                     160 tgc aag ccc tgt gcc ccg ggg acg ttc tcc aac acg act tca tcc acg      528
Cys Lys Pro Cys Ala Pro Gly Thr Phe Ser Asn Thr Thr Ser Ser Thr
                 165                     170                     175 gat att tgc agg ccc cac cag atc tgt aac gtg gtg gcc atc cct ggg      576
Asp Ile Cys Arg Pro His Gln Ile Cys Asn Val Val Ala Ile Pro Gly
             180                     185                     190 aat gca agc atg gat gca gtc tgc acg tcc acg tcc ccc acc cgg agt      624
Asn Ala Ser Met Asp Ala Val Cys Thr Ser Thr Ser Pro Thr Arg Ser
             195                     200                     205 atg gcc cca ggg gca gta cac tta ccc cag cca gtg tcc aca cga tcc      672
Met Ala Pro Gly Ala Val His Leu Pro Gln Pro Val Ser Thr Arg Ser
 210                     215                     220 caa cac acg cag cca act cca gaa ccc agc act gct cca agc acc tcc      720
Gln His Thr Gln Pro Thr Pro Glu Pro Ser Thr Ala Pro Ser Thr Ser
225                     230                     235                     240 ttc ctg ctc cca atg ggc ccc agc ccc cca gct gaa ggg agc act ggc      768
Phe Leu Leu Pro Met Gly Pro Ser Pro Pro Ala Glu Gly Ser Thr Gly
                 245                     250                     255 gac gag ccc aaa tct tgt gac aaa act cac aca tgc cca ccg tgc cca      816
Asp Glu Pro Lys Ser Cys Asp Lys Thr His Thr Cys Pro Pro Cys Pro
             260                     265                     270 gca cct gaa ctc ctg ggg gga ccg tca gtc ttc ctc ttc ccc cca aaa      864
Ala Pro Glu Leu Leu Gly Gly Pro Ser Val Phe Leu Phe Pro Pro Lys
             275                     280                     285 ccc aag gac acc ctc atg atc tcc cgg acc cct gag gtc aca tgc gtg      912
Pro Lys Asp Thr Leu Met Ile Ser Arg Thr Pro Glu Val Thr Cys Val
 290                     295                     300 gtg gtg gac gtg agc cac gaa gac cct gag gtc aag ttc aac tgg tac      960
Val Val Asp Val Ser His Glu Asp Pro Glu Val Lys Phe Asn Trp Tyr
305                     310                     315                     320 gtg gac ggc gtg gag gtg cat aat gcc aag aca aag ccg cgg gag gag     1008
Val Asp Gly Val Glu Val His Asn Ala Lys Thr Lys Pro Arg Glu Glu
                 325                     330                     335 cag tac aac agc acg tac cgt gtg gtc agc gtc ctc acc gtc ctg cac     1056
Gln Tyr Asn Ser Thr Tyr Arg Val Val Ser Val Leu Thr Val Leu His
```

-continued

```
                           340                 345                 350
cag gac tgg ctg aat ggc aag gag tac aag tgc aag gtc tcc aac aaa         1104
Gln Asp Trp Leu Asn Gly Lys Glu Tyr Lys Cys Lys Val Ser Asn Lys
            355                 360                 365 gcc ctc cca gcc ccc atc gag aaa acc atc tcc aaa gcc aaa ggg cag         1152
Ala Leu Pro Ala Pro Ile Glu Lys Thr Ile Ser Lys Ala Lys Gly Gln
        370                 375                 380 ccc cga gaa cca cag gtg tac acc ctg ccc cca tcc cgg gag gag atg         1200
Pro Arg Glu Pro Gln Val Tyr Thr Leu Pro Pro Ser Arg Glu Glu Met
385                 390                 395                 400 acc aag aac cag gtc agc ctg acc tgc ctg gtc aaa ggc ttc tat ccc         1248
Thr Lys Asn Gln Val Ser Leu Thr Cys Leu Val Lys Gly Phe Tyr Pro
                405                 410                 415 agc gac atc gcc gtg gag tgg gag agc aat ggg cag ccg gag aac aac         1296
Ser Asp Ile Ala Val Glu Trp Glu Ser Asn Gly Gln Pro Glu Asn Asn
            420                 425                 430 tac aag acc acg cct ccc gtg ctg gac tcc gac ggc tcc ttc ttc ctc         1344
Tyr Lys Thr Thr Pro Pro Val Leu Asp Ser Asp Gly Ser Phe Phe Leu
        435                 440                 445 tat agc aag ctc acc gtg gac aag agc agg tgg cag cag ggg aac gtc         1392
Tyr Ser Lys Leu Thr Val Asp Lys Ser Arg Trp Gln Gln Gly Asn Val
450                 455                 460 ttc tca tgc tcc gtg atg cat gag gct ctg cac aac cac tac acg cag         1440
Phe Ser Cys Ser Val Met His Glu Ala Leu His Asn His Tyr Thr Gln
465                 470                 475                 480 aag agc ctc tcc ctg tct ccg ggt aaa tga                                 1470
Lys Ser Leu Ser Leu Ser Pro Gly Lys
                485
```

<210> SEQ ID NO 2
<211> LENGTH: 489
<212> TYPE: PRT
<213> ORGANISM: Artificial Sequence
<220> FEATURE:
<223> OTHER INFORMATION: DNA encoding Enbrel, a recombinant fusion
      protein consisting of two soluble TNF receptors joined by the Fc
      fragment of a human IgG1 molecule

<400> SEQUENCE: 2

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160
```

```
Cys Lys Pro Cys Ala Pro Gly Thr Phe Ser Asn Thr Thr Ser Ser Thr
            165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
            210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
            245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
            290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
            370                 375                 380

Pro Arg Glu Pro Gln Val Tyr Thr Leu Pro Pro Ser Arg Glu Glu Met
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
            435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
            485

<210> SEQ ID NO 3
<211> LENGTH: 1470
<212> TYPE: DNA
<213> ORGANISM: Artificial Sequence
<220> FEATURE:
<223> OTHER INFORMATION: Codon modified Enbrel DNA

<400> SEQUENCE: 3
atggcgcccg tcgccgtctg ggccgcgctc gccgtcggac tcgaactctg ggctgcggcg      60
cacgccttgc cgcccaggt ggcatttaca ccctacgccc cggaacccgg aagcacatgc     120
cggctcagag aatactatga ccagacagct cagatgtgct gcagcaagtg ctcgccggga     180
caacacgcaa aggtcttttg tacaaagaca tcggacaccg tgtgtgactc ctgtgaggac     240
```

-continued

```
agcacataca cccagctctg gaactgggtt cccgagtgct tgagctgtgg ctcccgctgt      300
agctctgacc aggtggaaac tcaagcctgc actcgggaac agaaccgcat ctgcacctgc      360
aggcccggct ggtactgcgc gctgagcaag caggaggggt gccggctgtg cgcgccgctg      420
cgcaagtgcc gcccgggctt cggcgtggcc agaccaggaa ctgaaacatc agacgtggtg      480
tgcaagccct gtgccccggg gacgttctcc aacacgactt catccacgga tatttgcagg      540
ccccaccaga tctgtaacgt ggtggccatc cctgggaatg caagcatgga tgcagtctgc      600
acgtccacgt cccccacccg gagtatggcc caggggcag tacacttacc ccagccagtg       660
tccacacgat cccaacacac gcagccaact ccagaaccca gcactgctcc aagcacctcc      720
ttcctgctcc caatgggccc cagccccca gctgaaggga gcactggcga cgagcccaaa       780
tcttgtgaca aaactcacac atgcccaccg tgcccagcac ctgaactcct gggggaccg       840 tcagtcttcc tcttcccccc aaaacccaag gacaccctca tgatctcccg gacccctgag      900
gtcacatgcg tggtggtgga cgtgagccac gaagaccctg aggtcaagtt caactggtac      960
gtggacggcg tggaggtgca taatgccaag acaaagccgc gggaggagca gtacaacagc     1020
acgtaccgtg tggtcagcgt cctcaccgtc ctgcaccagg actggctgaa tggcaaggag     1080
tacaagtgca aggtctccaa caaagccctc ccagccccca tcgagaaaac catctccaaa     1140
gccaaagggc agccccgaga accacaggtg tacaccctgc ccccatcccg ggaggagatg     1200
accaagaacc aggtcagcct gacctgcctg gtcaaaggct tctatcccag cgacatcgcc     1260
gtggagtggg agagcaatgg gcagccggag aacaactaca agaccacgcc tcccgtgctg     1320
gactccgacg gctccttctt cctctatagc aagctcaccg tggacaagag caggtggcag     1380
caggggaacg tcttctcatg ctccgtgatg catgaggctc tgcacaacca ctacacgcag     1440
aagagcctct ccctgtctcc gggtaaatga                                      1470
```

```
<210> SEQ ID NO 4
<211> LENGTH: 297
<212> TYPE: DNA
<213> ORGANISM: Human papillomavirus type 16
<220> FEATURE:
<221> NAME/KEY: CDS
<222> LOCATION: (1)..(294)

<400> SEQUENCE: 4 atg cat gga gat aca cct aca ttg cat gaa tat atg tta gat ttg caa      48
Met His Gly Asp Thr Pro Thr Leu His Glu Tyr Met Leu Asp Leu Gln
1               5                   10                  15 cca gag aca act gat ctc tac tgt tat gag caa tta aat gac agc tca      96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac     144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg     192
Arg Ala His Tyr Asn Ile Val Thr Phe Cys Cys Lys Cys Asp Ser Thr
    50                  55                  60 ctt cgg ttg tgc gta caa agc aca cac gta gac att cgt act ttg gaa     240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct cag     288
Asp Leu Leu Met Gly Thr Leu Gly Ile Val Cys Pro Ile Cys Ser Gln
                85                  90                  95 aaa cca taa                                                         297
Lys Pro
```

<210> SEQ ID NO 5
<211> LENGTH: 98
<212> TYPE: PRT
<213> ORGANISM: Human papillomavirus type 16

<400> SEQUENCE: 5

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```

<210> SEQ ID NO 6
<211> LENGTH: 297
<212> TYPE: DNA
<213> ORGANISM: Artificial Sequence
<220> FEATURE:
<223> OTHER INFORMATION: Codon modified HPV16E7 DNA

<400> SEQUENCE: 6

```
atgcacggag atacccccac actccacgaa tatatgctcg atctccaacc cgaaacaaca      60
gatctctact gctatgaaca actcaacgat agctctgaag aagaagatga aatagatgga     120
ccagcaggac aagcagaacc cgatagagca cactacaaca ttgtaacatt ttgctgcaag     180
tgcgattcta cgctccggct ctgcgtacaa agcacacacg tagatattcg tacactcgaa     240
gatctcctca tgggaacact cggaattgtg tgccccatct gctctcagaa gccctaa       297
```

<210> SEQ ID NO 7
<211> LENGTH: 654
<212> TYPE: DNA
<213> ORGANISM: Human
<220> FEATURE:
<221> NAME/KEY: CDS
<222> LOCATION: (1)..(651)

<400> SEQUENCE: 7

```
atg gct aca ggc tcc cgg acg tcc ctg ctc ctg gct ttt ggc ctg ctc       48
Met Ala Thr Gly Ser Arg Thr Ser Leu Leu Leu Ala Phe Gly Leu Leu
1               5                   10                  15 tgc ctg ccc tgg ctt caa gag ggc agt gcc ttc cca acc att ccc tta       96
Cys Leu Pro Trp Leu Gln Glu Gly Ser Ala Phe Pro Thr Ile Pro Leu
                20                  25                  30 tcc agg cct ttt gac aac gct atg ctc cgc gcc cat cgt ctg cac cag      144
Ser Arg Pro Phe Asp Asn Ala Met Leu Arg Ala His Arg Leu His Gln
            35                  40                  45 ctg gcc ttt gac acc tac cag gag ttt gaa gaa gcc tat atc cca aag      192
Leu Ala Phe Asp Thr Tyr Gln Glu Phe Glu Glu Ala Tyr Ile Pro Lys
        50                  55                  60 gaa cag aag tat tca ttc ctg cag aac ccc cag acc tcc ctc tgt ttc      240
Glu Gln Lys Tyr Ser Phe Leu Gln Asn Pro Gln Thr Ser Leu Cys Phe
65                  70                  75                  80
```

```
tca gag tct att ccg aca ccc tcc aac agg gag gaa aca caa cag aaa    288
Ser Glu Ser Ile Pro Thr Pro Ser Asn Arg Glu Glu Thr Gln Gln Lys
            85                  90                  95 tcc aac cta gag ctg ctc cgc atc tcc ctg ctg ctc atc cag tcg tgg    336
Ser Asn Leu Glu Leu Leu Arg Ile Ser Leu Leu Leu Ile Gln Ser Trp
        100                 105                 110 ctg gag ccc gtg cag ttc ctc agg agt gtc ttc gcc aac agc ctg gtg    384
Leu Glu Pro Val Gln Phe Leu Arg Ser Val Phe Ala Asn Ser Leu Val
    115                 120                 125 tac ggc gcc tct gac agc aac gtc tat gac ctc cta aag gac cta gag    432
Tyr Gly Ala Ser Asp Ser Asn Val Tyr Asp Leu Leu Lys Asp Leu Glu
130                 135                 140 gaa ggc atc caa acg ctg atg ggg agg ctg gaa gat ggc agc ccc cgg    480
Glu Gly Ile Gln Thr Leu Met Gly Arg Leu Glu Asp Gly Ser Pro Arg
145                 150                 155                 160 act ggg cag atc ttc aag cag acc tac agc aag ttc gac aca aac tca    528
Thr Gly Gln Ile Phe Lys Gln Thr Tyr Ser Lys Phe Asp Thr Asn Ser
                165                 170                 175 cac aac gat gac gca cta ctc aag aac tac ggg ctg ctc tac tgc ttc    576
His Asn Asp Asp Ala Leu Leu Lys Asn Tyr Gly Leu Leu Tyr Cys Phe
            180                 185                 190 agg aag gac atg gac aag gtc gag aca ttc ctg cgc atc gtg cag tgc    624
Arg Lys Asp Met Asp Lys Val Glu Thr Phe Leu Arg Ile Val Gln Cys
        195                 200                 205 cgc tct gtg gag ggc agc tgt ggc ttc tag                            654
Arg Ser Val Glu Gly Ser Cys Gly Phe
    210                 215

<210> SEQ ID NO 8
<211> LENGTH: 217
<212> TYPE: PRT
<213> ORGANISM: Human

<400> SEQUENCE: 8

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Pro Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
        100                 105                 110

Leu Glu Pro Val Gln Phe Leu Arg Ser Val Phe Ala Asn Ser Leu Val
    115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190
```

```
Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 9
<211> LENGTH: 654
<212> TYPE: DNA
<213> ORGANISM: Artificial Sequence
<220> FEATURE:
<223> OTHER INFORMATION: Codon modified human growth hormone DNA

<400> SEQUENCE: 9
atggcaacag atctcggac  gtctctcctc ctcgcatttg gactcctctg cctcccctgg      60
ctccaagaag gaagcgcatt tcccacaatt cccctctcta gacccttga  taacgcaatg     120 ctccgggcac accgtctcca ccagctcgca tttgacacat accaggaatt gaagaagca      180 tatatcccca aggaacagaa gtattctttt ctgcagaacc cccagacctc cctctgtttc     240
tcagagtcta ttccgacacc ctccaacagg gaggaaacac aacagaaatc caacctagag     300
ctgctccgca tctccctgct gctcatccag tcgtggctgg agcccgtgca gttcctcagg     360
agtgtcttcg ccaacagcct ggtgtacggc gcctctgaca gcaacgtcta tgacctccta     420
aaggacctag aggaaggcat ccaaacgctg atggggaggc tggaagatgg cagccccgg     480 actgggcaga tcttcaagca gacctacagc aagttcgaca caaactcaca caacgatgac    540
gcactactca gaactacgg  gctgctctac tgcttcagga aggacatgga caaggtcgag     600
acattcctgc gcatcgtgca gtgccgctct gtggagggca gctgtggctt ctag           654

<210> SEQ ID NO 10
<211> LENGTH: 80
<212> TYPE: DNA
<213> ORGANISM: Artificial Sequence
<220> FEATURE:
<223> OTHER INFORMATION: Enbrel F1 oligonucleotide

<400> SEQUENCE: 10
catggcggcc cgtcgccgtc tgggccgcgc tcgccgtcgg actcgaactc tgggctgcgg      60
cacgccttgc ccgcccaggt                                                 80

<210> SEQ ID NO 11
<211> LENGTH: 77
<212> TYPE: DNA
<213> ORGANISM: Artificial Sequence
<220> FEATURE:
<223> OTHER INFORMATION: Enbrel R1 oligonucleotide

<400> SEQUENCE: 11
gggcgggcaa ggcgtgcgcc gcagcccaga gatcgagtcc gacggcgaag cgcggcccca      60
gacggcgcga cgggcgc                                                    77

<210> SEQ ID NO 12
<211> LENGTH: 78
<212> TYPE: DNA
<213> ORGANISM: Artificial Sequence
<220> FEATURE:
<223> OTHER INFORMATION: Enbrel F2 oligonucleotide

<400> SEQUENCE: 12
ggcatttaca ccctacgccc cggaacccgg aagcacatgc ggctcagag aatactatga      60 cagctcagat gtgctgca                                                   78
```

```
<210> SEQ ID NO 13
<211> LENGTH: 89
<212> TYPE: DNA
<213> ORGANISM: Artificial Sequence
<220> FEATURE:
<223> OTHER INFORMATION: Enbrel R2 oligonucleotide

<400> SEQUENCE: 13
gcacatctga gctgtctggt catagtattc tctgagccgg catgtgcttc cgggttccgg      60
gtccggggcg tagggtgtaa atgccacct                                       89

<210> SEQ ID NO 14
<211> LENGTH: 58
<212> TYPE: DNA
<213> ORGANISM: Artificial Sequence
<220> FEATURE:
<223> OTHER INFORMATION: Enbrel F3 oligonucleotide

<400> SEQUENCE: 14
gcaagtgctc gccgggacaa cacgcaaagg tcttttgtac aaagacatcg gacaccgt       58

<210> SEQ ID NO 15
<211> LENGTH: 59
<212> TYPE: DNA
<213> ORGANISM: Artificial Sequence
<220> FEATURE:
<223> OTHER INFORMATION: Enbrel R3 oligonucleotide

<400> SEQUENCE: 15
gtgtccgatg tctttgtaca aaagaccttt gcgtgttgtc ccggcgagca cttgctgca       59

<210> SEQ ID NO 16
<211> LENGTH: 86
<212> TYPE: DNA
<213> ORGANISM: Artificial Sequence
<220> FEATURE:
<223> OTHER INFORMATION: hGH F1 oligonucleotide

<400> SEQUENCE: 16
gatccaccat ggcaacagga tctcggacgt ctctcctcct cgcatttgga ctcctctgcc      60
tcccctggct ccaagaagaa ggaagc                                          86

<210> SEQ ID NO 17
<211> LENGTH: 70
<212> TYPE: DNA
<213> ORGANISM: Artificial Sequence
<220> FEATURE:
<223> OTHER INFORMATION: hGH R1 oligonucleotide

<400> SEQUENCE: 17
ttcttggagc caggggaggc agaggagtcc aaatgcgagg aggagagacg tccgagatcc      60
tgttgccatg                                                            70

<210> SEQ ID NO 18
<211> LENGTH: 80
<212> TYPE: DNA
<213> ORGANISM: Artificial Sequence
<220> FEATURE:
<223> OTHER INFORMATION: hGH F2 oligonucleotide

<400> SEQUENCE: 18
gcatttccca caattcccct cccctctcta gacccttga taacgcaatg ctccgggcac       60
accgtctcca ccagctcgca                                                 80
```

```
<210> SEQ ID NO 19
<211> LENGTH: 74
<212> TYPE: DNA
<213> ORGANISM: Artificial Sequence
<220> FEATURE:
<223> OTHER INFORMATION: hGH R2 oligonucleotide

<400> SEQUENCE: 19
tggtggagac ggtgtgcccg gagcattgcg ttatcaaagg gtctagagag gggaattgtg    60
ggaaatgcgc ttcc                                                      74

<210> SEQ ID NO 20
<211> LENGTH: 65
<212> TYPE: DNA
<213> ORGANISM: Artificial Sequence
<220> FEATURE:
<223> OTHER INFORMATION: hGH F3 oligonucleotide

<400> SEQUENCE: 20
tttgacacat accaggaatt tgaagaagca tatatcccca aggaacagaa gtattctttt    60
ctgca                                                                65

<210> SEQ ID NO 21
<211> LENGTH: 68
<212> TYPE: DNA
<213> ORGANISM: Artificial Sequence
<220> FEATURE:
<223> OTHER INFORMATION: hGH R3 oligonucleotide

<400> SEQUENCE: 21
gaaaagaata cttctgttcc ttggggatat atgcttcttc aaattcctgg tatgtgtcaa    60
atgcgagc                                                             68

<210> SEQ ID NO 22
<211> LENGTH: 97
<212> TYPE: DNA
<213> ORGANISM: Artificial Sequence
<220> FEATURE:
<223> OTHER INFORMATION: Genomic hGH F1 oligonucleotide

<400> SEQUENCE: 22
ccgggccaac atggctacag gatctcggac gtctctcctc ctcgcatttg gactcctctg    60 cctccctgg ctccaagaag gaagcgcatt tcccaca                              97

<210> SEQ ID NO 23
<211> LENGTH: 64
<212> TYPE: DNA
<213> ORGANISM: Artificial Sequence
<220> FEATURE:
<223> OTHER INFORMATION: Genomic hGH R1 oligonucleotide

<400> SEQUENCE: 23
gcgcggccag ctggtggaga cggtgtgccc ggagcattgc gttgtcaaag ggtctagaga    60
gggg                                                                 64

<210> SEQ ID NO 24
<211> LENGTH: 31
<212> TYPE: DNA
<213> ORGANISM: Artificial Sequence
<220> FEATURE:
<223> OTHER INFORMATION: Genomic hGH F2 oligonucleotide

<400> SEQUENCE: 24
```

-continued

```
cagctggcct ttgacacata ccaggaattt g                                    31
```

<210> SEQ ID NO 25
<211> LENGTH: 27
<212> TYPE: DNA
<213> ORGANISM: Artificial Sequence
<220> FEATURE:
<223> OTHER INFORMATION: Genomic hGH R2 oligonucleotide

<400> SEQUENCE: 25

```
cttcgggaaa aaccctgagc tccttag                                         27
```

<210> SEQ ID NO 26
<211> LENGTH: 1679
<212> TYPE: DNA
<213> ORGANISM: Human
<220> FEATURE:
<221> NAME/KEY: CDS
<222> LOCATION: (65)..(74)
<220> FEATURE:
<221> NAME/KEY: CDS
<222> LOCATION: (334)..(494)
<220> FEATURE:
<221> NAME/KEY: CDS
<222> LOCATION: (704)..(823)
<220> FEATURE:
<221> NAME/KEY: CDS
<222> LOCATION: (916)..(1080)
<220> FEATURE:
<221> NAME/KEY: CDS
<222> LOCATION: (1334)..(1528)

<400> SEQUENCE: 26

```
caaggatccc aaggcccaac tccccgaacc actcagggtc ctgtggacag ctcacctagc     60 tgca atg gct aca g gtaagcgccc ctaaaatccc tttggcacaa tgtgtcctga       114
     Met Ala Thr
       1 ggggagaggc agcgacctgt agatgggacg ggggcactaa ccctcaggtt tggggcttct   174 gaatgtgagt atcgccatgt aagcccagta tttggccaat ctcagaaagc tcctggtccc   234 tggagggatg gagagagaaa aacaaacagc tcctggagca gggagagtgc tggcctcttg   294 ctctccggct ccctctgttg ccctctggtt tctccccag gc  tcc cgg acg tcc      347
                                              Gly Ser Arg Thr Ser
                                                            5 ctg ctc ctg gct ttt ggc ctg ctc tgc ctg ccc tgg ctt caa gag ggc    395
Leu Leu Leu Ala Phe Gly Leu Leu Cys Leu Pro Trp Leu Gln Glu Gly
      10                  15                  20 agt gcc ttc cca acc att ccc tta tcc agg cct ttt gac aac gct atg    443
Ser Ala Phe Pro Thr Ile Pro Leu Ser Arg Pro Phe Asp Asn Ala Met
 25                  30                  35                  40 ctc cgc gcc cat cgt ctg cac cag ctg gcc ttt gac acc tac cag gag    491
Leu Arg Ala His Arg Leu His Gln Leu Ala Phe Asp Thr Tyr Gln Glu
                  45                  50                  55 ttt gtaagctctt gggaatgggg tgcgcatcag gggtggcagg aaggggtgac          544
Phe tttcccccgc tggaaataa gaggaggaga ctaaggagct cagggttttt cccgaagcga   604
aaatgcaggc agatgagcac acgctgagtg aggttcccag aaaagtaaca atgggagctg   664
gtctccagcg tagaccttgg tgggcggtcc ttctcctag gaa gaa gcc tat atc      718
                                             Glu Glu Ala Tyr Ile
                                                              60 cca aag gaa cag aag tat tca ttc ctg cag aac ccc cag acc tcc ctc    766
Pro Lys Glu Gln Lys Tyr Ser Phe Leu Gln Asn Pro Gln Thr Ser Leu
 65                  70                  75
```

```
                                                                         -continued
tgt ttc tca gag tct att ccg aca ccc tcc aac agg gag gaa aca caa          814
Cys Phe Ser Glu Ser Ile Pro Thr Pro Ser Asn Arg Glu Glu Thr Gln
 80                  85                  90 cag aaa tcc gtgagtggat gccttctccc caggcgggga tggggagac                   863
Gln Lys Ser
 95 ctgtagtcag agccccggg cagcacagcc aatgcccgtc cttcccctgc ag aac cta         921
                                                            Asn Leu gag ctg ctc cgc atc tcc ctg ctc atc cag tcg tgg ctg gag ccc              969
Glu Leu Leu Arg Ile Ser Leu Leu Ile Gln Ser Trp Leu Glu Pro
100                 105                 110                 115 gtg cag ttc ctc agg agt gtc ttc gcc aac agc ctg gtg tac ggc gcc         1017
Val Gln Phe Leu Arg Ser Val Phe Ala Asn Ser Leu Val Tyr Gly Ala
                120                 125                 130 tct gac agc aac gtc tat gac ctc cta aag gac cta gag gaa ggc atc         1065
Ser Asp Ser Asn Val Tyr Asp Leu Leu Lys Asp Leu Glu Glu Gly Ile
            135                 140                 145 caa acg ctg atg ggg gtgagggtgg cgccaggggt ccccaatcct ggagccccac         1120
Gln Thr Leu Met Gly
                150 tgactttgag agctgtgtta gagaaacact gctgccctct ttttagcagt caggccctga       1180
cccaagagaa ctcaccttat tcttcatttc ccctcgtgaa tcctccaggc ctttctctac       1240
accctgaagg ggaggagga aaatgaatga atgagaaagg gagggaacag tacccaagcg        1300
cttggcctct ccttctcttc cttcactttg cag agg ctg gaa gat ggc agc ccc        1354
                                   Arg Leu Glu Asp Gly Ser Pro
                                                    155 cgg act ggg cag atc ttc aag cag acc tac agc aag ttc gac aca aac         1402
Arg Thr Gly Gln Ile Phe Lys Gln Thr Tyr Ser Lys Phe Asp Thr Asn
160                 165                 170                 175 tca cac aac gat gac gca cta ctc aag aac tac ggg ctg ctc tac tgc         1450
Ser His Asn Asp Asp Ala Leu Leu Lys Asn Tyr Gly Leu Leu Tyr Cys
                180                 185                 190 ttc agg aag gac atg gac aag gtc gag aca ttc ctg cgc atc gtg cag         1498
Phe Arg Lys Asp Met Asp Lys Val Glu Thr Phe Leu Arg Ile Val Gln
            195                 200                 205 tgc cgc tct gtg gag ggc agc tgt ggc ttc tagctgcccg ggtggcatcc           1548
Cys Arg Ser Val Glu Gly Ser Cys Gly Phe
210                 215 ctgtgacccc tccccagtgc ctctcctggc cctggaagtt gccactccag tgcccaccag       1608
ccttgtccta ataaaattaa gttgcatcat tttgtctgac taggtgtcct tctataatat       1668
tatggggtgg a                                                            1679

<210> SEQ ID NO 27
<211> LENGTH: 217
<212> TYPE: PRT
<213> ORGANISM: Human

<400> SEQUENCE: 27

Met Ala Thr Gly Ser Arg Thr Ser Leu Leu Leu Ala Phe Gly Leu Leu
 1               5                   10                  15

Cys Leu Pro Trp Leu Gln Glu Gly Ser Ala Phe Pro Thr Ile Pro Leu
                20                  25                  30

Ser Arg Pro Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
```

```
            65                  70                  75                  80
Ser Glu Ser Ile Pro Thr Pro Ser Asn Arg Glu Glu Thr Gln Gln Lys
                    85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 28
<211> LENGTH: 1679
<212> TYPE: DNA
<213> ORGANISM: Artificial Sequence
<220> FEATURE:
<223> OTHER INFORMATION: Codon modified genomic hGH sequence

<400> SEQUENCE: 28
caaggatccc aaggcccaac tccccgaacc actcagggtc ctgtggacag ctcacctagc      60
tgcaatggct acaggtaagc gcccctaaaa tccctttggc acaatgtgtc ctgaggggag     120
aggcagcgac tgtagatgg gacggggca ctaaccctca ggtttgggc ttctgaatgt        180
gagtatcgcc atgtaagccc agtatttggc caatctcaga aagctcctgg tccctggagg    240
gatggagaga gaaaaacaaa cagctcctgg agcaggggaga gtgctggcct cttgctctcc    300
ggctccctct gttgccctct ggtttctccc caggatctcg gacgtctctc ctcctcgcat    360
ttggactcct ctgcctcccc tggctccaag aaggaagcgc atttcccaca attcccctct    420
ctagaccctt tgataacgca atgctccggg cacaccgtct ccaccagctg gcctttgaca    480
cataccagga atttgtaagc tcttggggaa tgggtgcgca tcaggggtgg caggaagggg    540
tgactttccc ccgctgggaa ataagaggag gagactaagg agctcagggt ttttcccgaa    600
gcgaaaatgc aggcagatga gcacacgctg agtgaggttc cagaaaagt aacaatggga    660
gctggtctcc agcgtagacc ttggtgggcg gtccttctcc taggaagaag cctatatccc    720
aaaggaacag aagtattcat tcctgcagaa ccccagacc tccctctgtt tctcagagtc     780
tattccgaca ccctccaaca gggaggaaac acaacagaaa tccgtgagtg gatgccttct    840
ccccaggcgg ggatggggga gacctgtagt cagagccccc gggcagcaca gccaatgccc    900
gtccttcccc tgcagaacct agagctgctc cgcatctccc tgctgctcat ccagtcgtgg    960
ctggagcccg tgcagttcct caggagtgtc ttcgccaaca gctggtgta cggcgcctct    1020
gacagcaacg tctatgacct cctaaaggac ctagaggaag catccaaac gctgatgggg    1080
gtgagggtgg cgccagggggt ccccaatcct ggagccccac tgactttgag agctgtgtta   1140
gagaaacact gctgccctct ttttagcagt caggccctga cccaagagaa ctcacccttat  1200
tcttcatttc ccctcgtgaa tcctccaggc ctttctctac accctgaagg ggaggaagga   1260
```

-continued

```
aaatgaatga atgagaaagg gagggaacag tacccaagcg cttggcctct ccttctcttc   1320
cttcactttg cagaggctgg aagatggcag cccccggact gggcagatct tcaagcagac   1380
ctacagcaag ttcgacacaa actcacacaa cgatgacgca ctactcaaga actacgggct   1440
gctctactgc ttcaggaagg acatggacaa ggtcgagaca ttcctgcgca tcgtgcagtg   1500
ccgctctgtg gagggcagct gtggcttcta gctgcccggg tggcatccct gtgacccctc   1560
cccagtgcct ctcctggccc tggaagttgc cactccagtg cccaccagcc ttgtcctaat   1620
aaaattaagt tgcatcattt tgtctgacta ggtgtccttc tataatatta tggggtgga   1679
```

GENE EXPRESSION SYSTEM BASED ON CODON TRANSLATION EFFICIENCY

CROSS-REFERENCE TO RELATED APPLICATIONS

This application is a continuation of International Patent Application No. PCT/AU2003/001200, filed Sep. 15, 2003, which claims priority of U.S. Provisional Patent Application No. 60/410,410, filed Sep. 13, 2002, the disclosures of all of which are hereby incorporated herein by reference.

BACKGROUND OF THE INVENTION

The present invention relates generally to gene expression. More particularly, the present invention relates to a method for modulating the production of a protein from a polynucleotide in a CHO cell by replacing at least one codon of the polynucleotide with a synonymous codon that has a higher or lower translation efficiency in the CHO cell than the codon it replaces, or by introducing into the CHO cell a polynucleotide that codes for an iso-tRNA which limits the rate of production of the polypeptide and which corresponds to a codon of the first polynucleotide. Even more particularly, the invention relates to the use of a protein-encoding polynucleotide whose codon composition has been modified for enhanced production of the protein in CHO cells.

The expression of foreign heterologous genes in transformed cells is now commonplace. A large number of mammalian genes, including, for example, murine and human genes, have been successfully expressed in various host cells, including bacterial, yeast, insect, plant and mammalian host cells. Nevertheless, despite the burgeoning knowledge of expression systems and recombinant DNA technology, significant obstacles remain when one attempts to express a foreign or synthetic gene in a selected host cell. For example, translation of a synthetic gene, even when coupled with a strong promoter, often proceeds much more slowly than would be expected. The same is frequently true of exogenous genes that are foreign to the host cell. This lower than expected translation efficiency is often due to the protein coding regions of the gene having a codon usage pattern that does not resemble those of highly expressed genes in the host cell. It is known in this regard that codon utilisation is highly biased and varies considerably in different organisms and that biases in codon usage can alter peptide elongation rates. It is also known that codon usage patterns are related to the relative abundance of tRNA isoacceptors, and that genes encoding proteins of high versus low abundance show differences in their codon preferences.

Codon-optimisation techniques have been developed for improving the translational kinetics of translationally inefficient protein coding regions. Traditionally, these techniques have been based on the replacement of codons that are rarely or infrequently used in the host cell with those that are host-preferred. Codon frequencies can be derived from literature sources for the highly expressed genes of many organisms (see, for example, Nakamura et al., 1996, *Nucleic Acids Res* 24: 214-215). These frequencies are generally expressed on an 'organism-wide average basis' as the percentage of occasions that a synonymous codon is used to encode a corresponding amino acid across a collection of protein-encoding genes of that organism, which are preferably highly expressed.

Typically, codons are classified as: (a) "common" codons (or "preferred" codons) if their frequency of usage is above about $4/3 \times$ the frequency of usage that would be expected in the absence of any bias in codon usage; (b) "rare" codons (or "non-preferred" codons) if their frequency of usage is below about $2/3 \times$ the frequency of usage that would be expected in the absence of any bias in codon usage; and (c) "intermediate" codons (or "less preferred" codons) if their frequency of usage is in-between the frequency of usage of "common" codons and of "rare" codons. Since an amino acid can be encoded by 2, 3, 4 or 6 codons, the frequency of usage of any selected codon, which would be expected in the absence of any bias in codon usage, will be dependent upon the number of synonymous codons which code for the same amino acid as the selected codon. Accordingly, for a particular amino acid, the frequency thresholds for classifying codons in the "common", "intermediate" and "rare" categories will be dependent upon the number of synonymous codons for that amino acid. Consequently, for amino acids having 6 choices of synonymous codon, the frequency of codon usage that would be expected in the absence of any bias in codon usage is 16% and thus the "common", "intermediate" and "rare" codons are defined as those codons that have a frequency of usage above 20%, between 10 and 20% and below 10%, respectively. For amino acids having 4 choices of synonymous codon, the frequency of codon usage that would be expected in the absence of codon usage bias is 25% and thus the "common", "intermediate" and "rare" codons are defined as those codons that have a frequency of usage above 33%, between 16 and 33% and below 16%, respectively. For isoleucine, which is the only amino acid having 3 choices of synonymous codon, the frequency of codon usage that would be expected in the absence of any bias in codon usage is 33% and thus the "common", "intermediate" and "rare" codons for isoleucine are defined as those codons that have a frequency of usage above 45%, between 20 and 45% and below 20%, respectively. For amino acids having 2 choices of synonymous codon, the frequency of codon usage that would be expected in the absence of codon usage bias is 50% and thus the "common," "intermediate" and "rare" codons are defined as those codons that have a frequency of usage above 60%, between 30 and 60% and below 30%, respectively. Thus, the categorisation of codons into the "common," "intermediate" and "rare" classes (or "preferred," "less preferred" or "non preferred," respectively) has been based conventionally on a compilation of codon usage for an organism in general (e.g., 'human-wide') or for a class of organisms in general (e.g., 'mammal-wide'). For example, reference may be made to Seed (see U.S. Pat. Nos. 5,786,464 and 5,795,737) who discloses preferred, less preferred and non-preferred codons for mammalian cells in general. However, the present inventor revealed in WO 99/02694 and in WO 00/42190 that there are substantial differences in the relative abundance of particular isoaccepting transfer RNAs in different cells or tissues of a single multicellular organism (e.g., a mammal or a plant) and that this plays a pivotal role in protein translation from a coding sequence with a given codon usage or composition.

Thus, in contrast to the art-recognised presumption that different cells of a multicellular organism have the same bias in codon usage, it was revealed for the first time that one cell type of a multicellular organism uses codons in a manner distinct from another cell type of the same organism. In other words, it was revealed that different cells of an organism can exhibit different translational efficiencies for the same codon and that it was not possible to predict which codons would be preferred, less preferred or non preferred in a selected cell type. Accordingly, it was proposed that differences in codon translational efficiency between cell types could be exploited, together with codon composition of a gene, to regulate the production of a protein in, or to direct that production to, a chosen cell type. Thus, in order to optimise the expression of a protein-encoding polynucleotide in a particular cell type it is necessary to first determine the translational efficiency for each codon in that cell type, rather than to rely on codon frequencies calculated on an organism-wide average basis, and then to codon modify the polynucleotide based on that determination.

BRIEF SUMMARY OF THE INVENTION

The present invention is predicated in part on the experimental determination of translational efficiency values for individual synonymous codons in Chinese Hamster Ovary (CHO) cells. Significantly, these values are not coterminous with the codon frequency values derivable from an analysis of the frequency with which codons are used to encode their corresponding amino acids across a collection of highly expressed mammalian protein-encoding genes, as for example disclosed by Seed (supra). As a result, the present invention enables for the first time the construction of protein-encoding polynucleotides, which are codon-optimised for efficient expression in CHO cells.

Thus, in one aspect of the present invention, there is provided a method of constructing a synthetic polynucleotide from which a polypeptide is producible at a different level in a Chinese Hamster Ovary (CHO) cell than from a parent polynucleotide encoding the same polypeptide, the method comprising:
  selecting a first codon of the parent polynucleotide for replacement with a synonymous codon, wherein the synonymous codon is selected on the basis that it exhibits a different translational efficiency in the CHO cell than the first codon in a comparison of translational efficiencies of codons in test CHO cells; and
  replacing the first codon with the synonymous codon to construct the synthetic polynucleotide,
wherein the comparison of translational efficiencies of the codons is represented by TABLE 1:

TABLE 1

| Codon | Translational Efficiency |
|---|---|
| Ala$^{GCA}$ | 38 |
| Ala$^{GCG}$ | 28 |
| Ala$^{GCT}$ | 18 |
| Ala$^{GCC}$ | 14 |
| Arg$^{AGA}$ | 36 |
| Arg$^{CGA}$ | 34 |
| Arg$^{CGG}$ | 35 |
| Arg$^{CGT}$ | 33 |
| Arg$^{AGG}$ | 29 |
| Arg$^{CGC}$ | 19 |
| Asn$^{AAC}$ | 40 |
| Asn$^{AAT}$ | 33 |
| Asp$^{GAT}$ | 27 |
| Asp$^{GAC}$ | 18 |
| Cys$^{TGC}$ | 32 |
| Cys$^{TGT}$ | 19 |
| Gln$^{CAA}$ | 18 |
| Gln$^{CAG}$ | 18 |
| Glu$^{GAA}$ | 16 |
| Glu$^{GAG}$ | 9 |
| Gly$^{GGA}$ | 60 |
| Gly$^{GGG}$ | 18 |
| Gly$^{GGC}$ | 12 |
| Gly$^{GGT}$ | 6 |
| His$^{CAC}$ | 32 |
| His$^{CAT}$ | 27 |
| Ile$^{ATC}$ | 8 |
| Ile$^{ATT}$ | 6 |

TABLE 1-continued

| Codon | Translational Efficiency |
|---|---|
| Ile$^{ATA}$ | 6 |
| Leu$^{CTC}$ | 45 |
| Leu$^{TTG}$ | 34 |
| Leu$^{CTA}$ | 25 |
| Leu$^{CTG}$ | 20 |
| Leu$^{TTA}$ | 18 |
| Leu$^{CTT}$ | 17 |
| Lys$^{AAG}$ | 28 |
| Lys$^{AAA}$ | 15 |
| Phe$^{TTT}$ | 30 |
| Phe$^{TTC}$ | 20 |
| Pro$^{CCC}$ | 70 |
| Pro$^{CCT}$ | 63 |
| Pro$^{CCG}$ | 60 |
| Pro$^{CCA}$ | 56 |
| Ser$^{AGC}$ | 72 |
| Ser$^{TCT}$ | 69 |
| Ser$^{AGT}$ | 65 |
| Ser$^{TCG}$ | 58 |
| Ser$^{TCA}$ | 58 |
| Ser$^{TCC}$ | 55 |
| Thr$^{ACA}$ | 47 |
| Thr$^{ACG}$ | 47 |
| Thr$^{ACT}$ | 45 |
| Thr$^{ACC}$ | 28 |
| Tyr$^{TAC}$ | 27 |
| Tyr$^{TAT}$ | 27 |
| Val$^{GTG}$ | 17 |
| Val$^{GTT}$ | 16 |
| Val$^{GTC}$ | 15 |
| Val$^{GTA}$ | 14 |

Thus, higher production of the polypeptide can be achieved by selecting a synonymous codon that has a higher translational efficiency than the first codon it replaces. In a preferred embodiment of this type, the synonymous codon is selected such that it has a translational efficiency in the CHO cell that is at least about 110% of the translational efficiency of the codon it replaces. In this embodiment, the first and synonymous codons are selected from TABLE 2:

TABLE 2

| First Codon | Synonymous Codon |
|---|---|
| Ala$^{GCG}$ | Ala$^{GCA}$ |
| Ala$^{GCT}$ | Ala$^{GCA}$ |
| Ala$^{GCC}$ | Ala$^{GCA}$ |
| Ala$^{GCT}$ | Ala$^{GCG}$ |
| Ala$^{GCC}$ | Ala$^{GCG}$ |
| Ala$^{GCC}$ | Ala$^{GCT}$ |
| Arg$^{CGT}$ | Arg$^{AGA}$ |
| Arg$^{AGG}$ | Arg$^{AGA}$ |
| Arg$^{CGC}$ | Arg$^{AGA}$ |
| Arg$^{CGT}$ | Arg$^{CGA}$ |
| Arg$^{AGG}$ | Arg$^{CGA}$ |
| Arg$^{CGC}$ | Arg$^{CGA}$ |
| Arg$^{AGG}$ | Arg$^{CGG}$ |
| Arg$^{CGC}$ | Arg$^{CGG}$ |
| Arg$^{AGG}$ | Arg$^{CGT}$ |
| Arg$^{CGC}$ | Arg$^{CGT}$ |
| Arg$^{CGC}$ | Arg$^{AGG}$ |
| Asn$^{AAT}$ | Asn$^{AAC}$ |
| Asp$^{GAC}$ | Asp$^{GAT}$ |
| Cys$^{TGT}$ | Cys$^{TGC}$ |
| Glu$^{GAG}$ | Glu$^{GAA}$ |
| Gly$^{GGG}$ | Gly$^{GGA}$ |
| Gly$^{GGC}$ | Gly$^{GGA}$ |
| Gly$^{GGT}$ | Gly$^{GGA}$ |
| Gly$^{GGC}$ | Gly$^{GGG}$ |
| Gly$^{GGT}$ | Gly$^{GGG}$ |
| Gly$^{GGT}$ | Gly$^{GGC}$ |

TABLE 2-continued

| First Codon | Synonymous Codon |
|---|---|
| His$^{CAT}$ | His$^{CAC}$ |
| Ile$^{ATT}$ | Ile$^{ATC}$ |
| Ile$^{ATA}$ | Ile$^{ATC}$ |
| Leu$^{TTG}$ | Leu$^{CTC}$ |
| Leu$^{CTA}$ | Leu$^{CTC}$ |
| Leu$^{CTG}$ | Leu$^{CTC}$ |
| Leu$^{TTA}$ | Leu$^{CTC}$ |
| Leu$^{CTT}$ | Leu$^{CTC}$ |
| Leu$^{CTA}$ | Leu$^{TTG}$ |
| Leu$^{CTG}$ | Leu$^{TTG}$ |
| Leu$^{TTA}$ | Leu$^{TTG}$ |
| Leu$^{CTT}$ | Leu$^{TTG}$ |
| Leu$^{CTG}$ | Leu$^{CTA}$ |
| Leu$^{TTA}$ | Leu$^{CTA}$ |
| Leu$^{CTT}$ | Leu$^{CTA}$ |
| Leu$^{TTA}$ | Leu$^{CTG}$ |
| Leu$^{CTT}$ | Leu$^{CTG}$ |
| Leu$^{CTT}$ | Leu$^{TTA}$ |
| Lys$^{AAA}$ | Lys$^{AAG}$ |
| Phe$^{TTC}$ | Phe$^{TTT}$ |
| Pro$^{CCT}$ | Pro$^{CCC}$ |
| Pro$^{CCG}$ | Pro$^{CCC}$ |
| Pro$^{CCA}$ | Pro$^{CCC}$ |
| Pro$^{CCG}$ | Pro$^{CCT}$ |
| Pro$^{CCA}$ | Pro$^{CCT}$ |
| Pro$^{CCA}$ | Pro$^{CCG}$ |
| Ser$^{AGT}$ | Ser$^{AGC}$ |
| Ser$^{TCG}$ | Ser$^{AGC}$ |
| Ser$^{TCA}$ | Ser$^{AGC}$ |
| Ser$^{TCC}$ | Ser$^{AGC}$ |
| Ser$^{TCG}$ | Ser$^{TCT}$ |
| Ser$^{TCA}$ | Ser$^{TCT}$ |
| Ser$^{TCC}$ | Ser$^{TCT}$ |
| Ser$^{TCG}$ | Ser$^{AGT}$ |
| Ser$^{TCA}$ | Ser$^{AGT}$ |
| Ser$^{TCC}$ | Ser$^{AGT}$ |
| Ser$^{TCC}$ | Ser$^{TCG}$ |
| Ser$^{TCC}$ | Ser$^{TCA}$ |
| Thr$^{ACC}$ | Thr$^{ACA}$ |
| Thr$^{ACC}$ | Thr$^{ACG}$ |
| Thr$^{ACC}$ | Thr$^{ACT}$ |
| Val$^{GTC}$ | Val$^{GTG}$ |
| Val$^{GTA}$ | Val$^{GTG}$ |
| Val$^{GTA}$ | Val$^{GTT}$ |

Conversely, low production can be achieved by selecting a synonymous codon that has a lower translational efficiency than the first codon it replaces. In a preferred embodiment of this type, the synonymous codon is selected such that it has a translational efficiency in the CHO cell that is less than about 90% of the translational efficiency of the codon it replaces. In this embodiment, the first and synonymous codons are selected from the TABLE 3:

TABLE 3

| First Codon | Synonymous Codon |
|---|---|
| Ala$^{GCA}$ | Ala$^{GCG}$ |
| Ala$^{GCA}$ | Ala$^{GCT}$ |
| Ala$^{GCA}$ | Ala$^{GCC}$ |
| Ala$^{GCG}$ | Ala$^{GCT}$ |
| Ala$^{GCG}$ | Ala$^{GCC}$ |
| Ala$^{GCT}$ | Ala$^{GCC}$ |
| Arg$^{AGA}$ | Arg$^{CGT}$ |
| Arg$^{AGA}$ | Arg$^{AGG}$ |
| Arg$^{AGA}$ | Arg$^{CGC}$ |
| Arg$^{CGA}$ | Arg$^{CGT}$ |
| Arg$^{CGA}$ | Arg$^{AGG}$ |
| Arg$^{CGA}$ | Arg$^{CGC}$ |
| Arg$^{CGG}$ | Arg$^{AGG}$ |
| Arg$^{CGG}$ | Arg$^{CGC}$ |
| Arg$^{CGT}$ | Arg$^{AGG}$ |

TABLE 3-continued

| First Codon | Synonymous Codon |
|---|---|
| Arg$^{CGT}$ | Arg$^{CGC}$ |
| Arg$^{AGG}$ | Arg$^{CGC}$ |
| Asn$^{AAC}$ | Asn$^{AAT}$ |
| Asp$^{GAT}$ | Asp$^{GAC}$ |
| Cys$^{TGC}$ | Cys$^{TGT}$ |
| Glu$^{GAA}$ | Glu$^{GAG}$ |
| Gly$^{GGA}$ | Gly$^{GGG}$ |
| Gly$^{GGA}$ | Gly$^{GGC}$ |
| Gly$^{GGA}$ | Gly$^{GGT}$ |
| Gly$^{GGG}$ | Gly$^{GGC}$ |
| Gly$^{GGG}$ | Gly$^{GGT}$ |
| Gly$^{GGC}$ | Gly$^{GGT}$ |
| His$^{CAC}$ | His$^{CAT}$ |
| Ile$^{ATC}$ | Ile$^{ATT}$ |
| Ile$^{ATC}$ | Ile$^{ATA}$ |
| Leu$^{CTC}$ | Leu$^{TTG}$ |
| Leu$^{CTC}$ | Leu$^{CTA}$ |
| Leu$^{CTC}$ | Leu$^{CTG}$ |
| Leu$^{CTC}$ | Leu$^{TTA}$ |
| Leu$^{CTC}$ | Leu$^{CTT}$ |
| Leu$^{TTG}$ | Leu$^{CTA}$ |
| Leu$^{TTG}$ | Leu$^{CTG}$ |
| Leu$^{TTG}$ | Leu$^{TTA}$ |
| Leu$^{TTG}$ | Leu$^{CTT}$ |
| Leu$^{CTA}$ | Leu$^{CTG}$ |
| Leu$^{CTA}$ | Leu$^{TTA}$ |
| Leu$^{CTA}$ | Leu$^{CTT}$ |
| Leu$^{CTG}$ | Leu$^{TTA}$ |
| Leu$^{CTG}$ | Leu$^{CTT}$ |
| Leu$^{TTA}$ | Leu$^{CTT}$ |
| Lys$^{AAG}$ | Lys$^{AAA}$ |
| Phe$^{TTT}$ | Phe$^{TTC}$ |
| Pro$^{CCC}$ | Pro$^{CCT}$ |
| Pro$^{CCC}$ | Pro$^{CCG}$ |
| Pro$^{CCC}$ | Pro$^{CCA}$ |
| Pro$^{CCT}$ | Pro$^{CCG}$ |
| Pro$^{CCT}$ | Pro$^{CCA}$ |
| Pro$^{CCG}$ | Pro$^{CCA}$ |
| Ser$^{AGC}$ | Ser$^{AGT}$ |
| Ser$^{AGC}$ | Ser$^{TCG}$ |
| Ser$^{AGC}$ | Ser$^{TCA}$ |
| Ser$^{AGC}$ | Ser$^{TCC}$ |
| Ser$^{TCT}$ | Ser$^{TCG}$ |
| Ser$^{TCT}$ | Ser$^{TCA}$ |
| Ser$^{TCT}$ | Ser$^{TCC}$ |
| Ser$^{AGT}$ | Ser$^{TCG}$ |
| Ser$^{AGT}$ | Ser$^{TCA}$ |
| Ser$^{AGT}$ | Ser$^{TCC}$ |
| Ser$^{TCG}$ | Ser$^{TCC}$ |
| Ser$^{TCA}$ | Ser$^{TCC}$ |
| Thr$^{ACA}$ | Thr$^{ACC}$ |
| Thr$^{ACG}$ | Thr$^{ACC}$ |
| Thr$^{ACT}$ | Thr$^{ACC}$ |
| Val$^{GTG}$ | Val$^{GTC}$ |
| Val$^{GTG}$ | Val$^{GTA}$ |
| Val$^{GTT}$ | Val$^{GTA}$ |

In an especially preferred embodiment, the comparison of translational efficiencies of the codons is represented by TABLE 4:

TABLE 4

| | Translational Efficiency | |
|---|---|---|
| High | Intermediate | Low |
| Ala$^{GCA}$ | Ala$^{GCG}$, Ala$^{GCT}$ | Ala$^{GCC}$ |
| | Arg$^{AGA}$, Arg$^{CGA}$, ARG$^{CGG}$, Arg$^{CGT}$, Arg$^{AGG}$ | Arg$^{CGC}$ |
| Asn$^{AAC}$ | | Asn$^{AAT}$ |
| Asp$^{GAT}$ | | Asp$^{GAC}$ |
| Cys$^{TGC}$ | | Cys$^{TGT}$ |
| Glu$^{GAA}$ | | Glu$^{GAG}$ |
| | Gln$^{CAA}$, Gln$^{CAG}$ | |

TABLE 4-continued

| Translational Efficiency | | |
|---|---|---|
| High | Intermediate | Low |
| Gly$^{GGA}$ | Gly$^{GGG}$ | Gly$^{GGC}$, Gly$^{GGT}$ |
| His$^{CAC}$ | | His$^{CAT}$ |
| | Ile$^{ATT}$, Ile$^{ATC}$, Ile$^{ATA}$ | |
| Leu$^{CTC}$, Leu$^{TTG}$ | Leu$^{CTA}$, Leu$^{CTG}$ | Leu$^{TTA}$, Leu$^{CTT}$ |
| Lys$^{AAG}$ | | Lys$^{AAA}$ |
| Phe$^{TTT}$ | | Phe$^{TTC}$ |
| | Pro$^{CCC}$, Pro$^{CCT}$, Pro$^{CCG}$, Pro$^{CCA}$ | |
| | Ser$^{AGC}$, Ser$^{TCT}$, Ser$^{AGT}$, Ser$^{TCG}$, Ser$^{TCA}$, Ser$^{TCC}$ | |
| | Thr$^{ACA}$, Thr$^{ACG}$, Thr$^{ACT}$ | Thr$^{ACC}$ |
| | Tyr$^{TAC}$, Tyr$^{TAT}$ | |
| | Val$^{GTA}$, Val$^{GTT}$, Val$^{GTC}$, Val$^{GTG}$ | |

Thus, another aspect of the present invention contemplates a method of constructing a synthetic polynucleotide from which a polypeptide is producible at a higher level in a Chinese Hamster Ovary (CHO) cell than from a parent polynucleotide encoding the same polypeptide, the method comprising:

selecting a first codon of the parent polynucleotide for replacement with a synonymous codon, wherein the synonymous codon is selected on the basis that it exhibits a higher translational efficiency in the CHO cell than the first codon in a comparison of translational efficiencies of codons in test CHO cells; and replacing the first codon with the synonymous codon to construct the synthetic polynucleotide, wherein the first and synonymous codons are selected from TABLE 5:

TABLE 5

| First Codon | Synonymous Codon |
|---|---|
| Ala$^{GCC}$ | Ala$^{GCA}$ |
| Ala$^{GCC}$ | Ala$^{GCG}$ |
| Ala$^{GCC}$ | Ala$^{GCT}$ |
| Ala$^{GCT}$ | Ala$^{GCA}$ |
| Ala$^{GCG}$ | Ala$^{GCA}$ |
| Arg$^{CGC}$ | Arg$^{AGA}$ |
| Arg$^{CGC}$ | Arg$^{CGA}$ |
| Arg$^{CGC}$ | Arg$^{CGG}$ |
| Arg$^{CGC}$ | Arg$^{CGT}$ |
| Arg$^{CGC}$ | Arg$^{AGG}$ |
| Asn$^{AAT}$ | Asn$^{AAC}$ |
| Asp$^{GAC}$ | Asp$^{GAT}$ |
| Cys$^{TGT}$ | Cys$^{TGC}$ |
| Glu$^{GAG}$ | Glu$^{GAA}$ |
| Gly$^{GGT}$ | Gly$^{GGA}$ |
| Gly$^{GGT}$ | Gly$^{GGG}$ |
| Gly$^{GGC}$ | Gly$^{GGA}$ |
| Gly$^{GGC}$ | Gly$^{GGG}$ |
| Gly$^{GGG}$ | Gly$^{GGA}$ |
| His$^{CAT}$ | His$^{CAC}$ |
| Leu$^{CTT}$ | Leu$^{CTC}$ |
| Leu$^{CTT}$ | Leu$^{TTG}$ |
| Leu$^{TTA}$ | Leu$^{CTC}$ |
| Leu$^{TTA}$ | Leu$^{TTG}$ |
| Leu$^{CTG}$ | Leu$^{CTC}$ |
| Leu$^{CTG}$ | Leu$^{TTG}$ |
| Leu$^{CTA}$ | Leu$^{CTC}$ |
| Leu$^{CTA}$ | Leu$^{TTG}$ |
| Lys$^{AAA}$ | Lys$^{AAG}$ |
| Phe$^{TTC}$ | Phe$^{TTT}$ |

In yet another aspect, the invention contemplates a method of constructing a synthetic polynucleotide from which a polypeptide is producible at a lower level in a Chinese Hamster Ovary (CHO) cell than from a parent polynucleotide encoding the same polypeptide, the method comprising:

selecting a first codon of the parent polynucleotide for replacement with a synonymous codon, wherein the synonymous codon is selected on the basis that it exhibits a lower translational efficiency in the CHO cell than the first codon in a comparison of translational efficiencies of codons in test CHO cells; and replacing the first codon with the synonymous codon to construct the synthetic polynucleotide, wherein the first and synonymous codons are selected from TABLE 6:

TABLE 6

| First Codon | Synonymous Codon |
|---|---|
| Ala$^{GCA}$ | Ala$^{GCC}$ |
| Ala$^{GCG}$ | Ala$^{GCC}$ |
| Ala$^{GCT}$ | Ala$^{GCC}$ |
| Ala$^{GCA}$ | Ala$^{GCT}$ |
| Ala$^{GCA}$ | Ala$^{GCG}$ |
| Arg$^{AGA}$ | Arg$^{CGC}$ |
| Arg$^{CGA}$ | Arg$^{CGC}$ |
| Arg$^{CGG}$ | Arg$^{CGC}$ |
| Arg$^{CGT}$ | Arg$^{CGC}$ |
| Arg$^{AGG}$ | Arg$^{CGC}$ |
| Asn$^{AAC}$ | Asn$^{AAT}$ |
| Asp$^{GAT}$ | Asp$^{GAC}$ |
| Cys$^{TGC}$ | Cys$^{TGT}$ |
| Glu$^{GAA}$ | Glu$^{GAG}$ |
| Gly$^{GGA}$ | Gly$^{GGT}$ |
| Gly$^{GGG}$ | Gly$^{GGT}$ |
| Gly$^{GGA}$ | Gly$^{GGC}$ |
| Gly$^{GGG}$ | Gly$^{GGC}$ |
| Gly$^{GGA}$ | Gly$^{GGG}$ |
| His$^{CAC}$ | His$^{CAT}$ |
| Leu$^{CTC}$ | Leu$^{CTT}$ |
| Leu$^{TTG}$ | Leu$^{CTT}$ |
| Leu$^{CTC}$ | Leu$^{TTA}$ |
| Leu$^{TTG}$ | Leu$^{TTA}$ |
| Leu$^{CTC}$ | Leu$^{CTG}$ |
| Leu$^{TTG}$ | Leu$^{CTG}$ |
| Leu$^{CTC}$ | Leu$^{CTA}$ |
| Leu$^{TTG}$ | Leu$^{CTA}$ |
| Lys$^{AAG}$ | Lys$^{AAA}$ |
| Phe$^{TTT}$ | Phe$^{TTC}$ |

In yet another aspect, the invention provides a synthetic polynucleotide constructed according to any one of the above methods.

In still another aspect, the invention embraces a method of modifying a Chinese Hamster Ovary (CHO) cell so that a polypeptide is producible at a higher level from a first polynucleotide, the method comprising:

introducing into the CHO cell a second polynucleotide encoding an iso-tRNA which limits the rate of production of the polypeptide and which corresponds to a codon of the first polynucleotide, wherein the codon is selected from the group consisting of Ala$^{GCC}$, Ala$^{GCT}$, Ala$^{GCG}$, Arg$^{AGA}$, Arg$^{CGG}$, Arg$^{CGA}$, Arg$^{CGT}$, Arg$^{AGG}$, Arg$^{CGC}$, Asn$^{AAC}$, Asn$^{AAT}$, Asp$^{GAC}$, Cys$^{TGT}$, Glu$^{GAG}$, Gln$^{CAA}$, Gln$^{CAG}$, Gly$^{GGC}$, Gly$^{GGG}$, Gly$^{GGT}$, His$^{CAC}$, His$^{CAT}$, Ile$^{ATT}$, Ile$^{ATC}$, Ile$^{ATA}$, Leu$^{CTA}$, Leu$^{CTG}$, Leu$^{TTA}$, Leu$^{CTT}$, Lys$^{AAA}$, Phe$^{TTT}$, Phe$^{TTC}$, Pro$^{CCC}$, Pro$^{CCA}$, Pro$^{CCG}$, Pro$^{CCT}$, Ser$^{AGC}$, Ser$^{TCT}$, Ser$^{AGT}$, Ser$^{TCG}$, Ser$^{TCA}$, Ser$^{TCC}$, Thr$^{ACA}$, Thr$^{ACG}$, Thr$^{ACT}$, Thr$^{ACC}$, Tyr$^{TAC}$, Tyr$^{TAT}$, Val$^{GTA}$, Val$^{GTT}$, Val$^{GTC}$ and Val$^{GTG}$, wherein the second polynucleotide is operably linked to a regulatory polynucleotide.

In a preferred embodiment, the iso-tRNA corresponds to a codon that is selected from the group consisting of Ala$^{GCC}$, Arg$^{CGC}$, Asp$^{GAC}$, Cys$^{TGT}$, Glu$^{GAG}$, Gly$^{GGC}$, Gly$^{GGG}$, Gly$^{GGT}$, Leu$^{TTA}$, Leu$^{CTT}$, Lys$^{AAA}$ and Thr$^{ACC}$.

In yet another aspect, the invention provides a modified Chinese Hamster Ovary (CHO) cell resulting from the above method.

In a further aspect, the invention encompasses a method of producing a polypeptide in a Chinese Hamster Ovary (CHO) cell from a synthetic polynucleotide at a different level than from a parent polynucleotide encoding the same polypeptide, the method comprising:
  selecting a first codon of the parent polynucleotide for replacement with a synonymous codon, wherein the synonymous codon is selected on the basis that it exhibits a different translational efficiency in the CHO cell than the first codon in a comparison of translational efficiencies of codons in test CHO cells as represented by TABLE 1 or by TABLE 4;
  replacing the first codon with the synonymous codon to construct the synthetic polynucleotide;
  introducing the synthetic polynucleotide into the CHO cell; and
  expressing the synthetic polynucleotide in the CHO cell, whereby the polypeptide is produced from the synthetic polynucleotide in the CHO cell at a different level than from the parent polynucleotide.

In yet a further aspect, the invention features a method of producing a polypeptide in a Chinese Hamster Ovary (CHO) cell from a synthetic polynucleotide at a higher level than from a parent polynucleotide encoding the same polypeptide, the method comprising:
  selecting a first codon of the parent polynucleotide for replacement with a synonymous codon, wherein the synonymous codon is selected on the basis that it exhibits a higher translational efficiency in the CHO cell than the first codon in a comparison of translational efficiencies of codons in test CHO cells, wherein both the first and synonymous codons are selected from TABLE 2 or from TABLE 5;
  replacing the first codon with the synonymous codon to construct the synthetic polynucleotide;
  introducing the synthetic polynucleotide into the CHO cell; and
  expressing the synthetic polynucleotide in the CHO cell, whereby the polypeptide is produced from the synthetic polynucleotide in the CHO cell at a higher level than from the parent polynucleotide.

In still a further aspect, the invention features a method of producing a polypeptide in a Chinese Hamster Ovary (CHO) cell from a synthetic polynucleotide at a lower level than from a parent polynucleotide encoding the same polypeptide, the method comprising:
  selecting a first codon of the parent polynucleotide for replacement with a synonymous codon, wherein the synonymous codon is selected on the basis that it exhibits a lower translational efficiency in the CHO cell than the first codon in a comparison of translational efficiencies of codons in test CHO cells, wherein the both first and synonymous codons are selected from TABLE 3 or from TABLE 6;
  replacing the first codon with the synonymous codon to construct the synthetic polynucleotide;
  introducing the synthetic polynucleotide into the CHO cell; and
  expressing the synthetic polynucleotide in the CHO cell, whereby the polypeptide is produced from the synthetic polynucleotide in the CHO cell at a lower level than from the parent polynucleotide.

In some embodiments, the above methods further comprise isolating or purifying the polypeptide from the CHO cell.

In another aspect, the invention provides a polypeptide produced according to any one of the above methods.

In still another aspect, the invention extends to a method of producing a virus particle in a Chinese Hamster Ovary (CHO) cell, wherein the virus particle comprises a polypeptide necessary for assembly of the virus particle, and wherein the polypeptide is produced in the CHO cell from a parent polynucleotide, but not at a level sufficient to permit productive virus assembly therein, the method comprising:
  selecting a first codon of the parent polynucleotide for replacement with a synonymous codon, wherein the synonymous codon is selected on the basis that it exhibits a higher translational efficiency in the CHO cell than the first codon in a comparison of translational efficiencies of codons in test CHO cells as represented by TABLE 1 or by TABLE 4;
  replacing the first codon with the synonymous codon to construct the synthetic polynucleotide; and
  introducing into the CHO cell the synthetic polynucleotide operably linked to a regulatory polynucleotide,
whereby the synthetic polynucleotide is expressed to produce the polypeptide at a level sufficient to permit the production of the virus particle in the CHO cell.

In a further aspect, the invention extends to a method of producing a virus particle in a Chinese Hamster Ovary (CHO) cell, wherein the virus particle comprises a polypeptide necessary for assembly of the virus particle, and wherein the polypeptide is produced in the CHO cell from a parent polynucleotide, but not at a level sufficient to permit productive virus assembly therein, the method comprising:
  selecting a first codon of the parent polynucleotide for replacement with a synonymous codon, wherein the synonymous codon is selected on the basis that it exhibits a higher translational efficiency in the CHO cell than the first codon in a comparison of translational efficiencies of codons in test CHO, wherein both the first and synonymous codons are selected from TABLE 2 or from TABLE 5;
  replacing the first codon with the synonymous codon to construct the synthetic polynucleotide; and
  introducing into the CHO cell the synthetic polynucleotide operably linked to a regulatory polynucleotide,
whereby the synthetic polynucleotide is expressed to produce the polypeptide at a level sufficient to permit the production of the virus particle in the CHO cell.

In still another aspect, the invention provides a method of producing a virus particle in a Chinese Hamster Ovary (CHO) cell, wherein the virus particle comprises at least one polypeptide necessary for assembly of the virus particle, wherein the polypeptide is produced in the CHO cell from a first polynucleotide, but not at a level sufficient to permit productive virus assembly therein, and wherein the abundance of an iso-tRNA specific for a codon of the first polynucleotide limits the rate of production of the polypeptide and corresponds to a codon that is selected from the group consisting Ala$^{GCC}$, Ala$^{GCT}$, Ala$^{GCG}$, Arg$^{CGC}$, Asn$^{AAT}$, Asp$^{GAC}$, Cys$^{TGT}$, Glu$^{GAG}$, Gln$^{CAA}$, Gly$^{GGT}$, Gly$^{GGC}$, Gly$^{GGG}$, His$^{CAT}$, Leu$^{CTT}$, Leu$^{TTA}$, Leu$^{CTG}$, Leu$^{CTA}$, Lys$^{AAA}$, Phe$^{TTC}$, the method comprising:
  introducing into the CHO cell a second polynucleotide, which encodes the iso-tRNA and which is operably linked to a regulatory polynucleotide, whereby the second polynucleotide is expressed to produce the iso-tRNA at a level sufficient to increase the rate of production of the polypeptide to thereby permit the production of the virus particle in the CHO cell.

In some embodiments, the above methods further comprise isolating or purifying the virus particle from the CHO cell.

In another aspect, the invention provides a virus particle produced according to any one of the above methods.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 is a diagrammatic representation depicting a parent nucleotide sequence [SEQ ID NO:1] that codes for Enbrel® (also known as etanercept), a recombinant fusion protein consisting of two soluble TNF receptors joined by the Fc fragment of a human IgG1 molecule, whose amino acid sequence is set forth in SEQ ID NO:2. Mutations introduced into the parent nucleotide sequence to produce a codon-modified Enbrel® nucleotide sequence [SEQ ID NO:3] are indicated below the corresponding nucleotides of the parent sequence. Replacement of these nucleotides results in a nucleic acid sequence encoding the same amino acid sequence as the parent Enbrel® nucleotide sequence, but having synonymous codons that have a higher translational efficiency in CHO cells than the codons they replaced.

FIG. 2 is a diagrammatic representation depicting a wild-type nucleotide sequence [SEQ ID NO:4] that codes for human papillomavirus (HPV) type 16 E7 protein, whose amino acid sequence is set forth in SEQ ID NO:5. Mutations introduced into the wild-type sequence to produce a codon-modified HPV16E7 nucleotide sequence [SEQ ID NO:6] are indicated below the corresponding nucleotides of the wild-type sequence. Replacement of these nucleotides results in a nucleic acid sequence encoding the same amino acid sequence as the wild-type HPV16E7 nucleotide sequence, but having synonymous codons that have a higher translational efficiency in CHO cells than the codons they replaced.

FIG. 3 is a diagrammatic representation depicting a wild-type cDNA sequence [SEQ ID NO:7] that codes for human growth hormone (hGH), whose amino acid sequence is set forth in SEQ ID NO:8. Mutations introduced into the wild-type sequence to produce a codon-modified hGH nucleotide sequence are indicated below the corresponding nucleotides of the wild-type sequence. Replacement of these nucleotides results in a nucleic acid sequence encoding the same amino acid sequence as the wild-type hGH nucleotide sequence, but having synonymous codons that have a higher translational efficiency in CHO cells than the codons they replaced.

FIG. 4 is a diagrammatic representation showing a wild-type genomic sequence [SEQ ID NO:26] that codes for human growth hormone (hGH), whose amino acid sequence is set forth in SEQ ID NO:8 or 27. Mutations introduced into the wild-type sequence to produce a codon-modified hGH genomic sequence are indicated below the corresponding nucleotides of the wild-type sequence. Replacement of these nucleotides results in a modified genomic sequence encoding the same amino acid sequence as the wild-type genomic sequence, but having synonymous codons that have a higher translational efficiency in CHO cells than the codons they replaced.

BRIEF DESCRIPTION OF THE SEQUENCES

TABLE A

Figure 5:
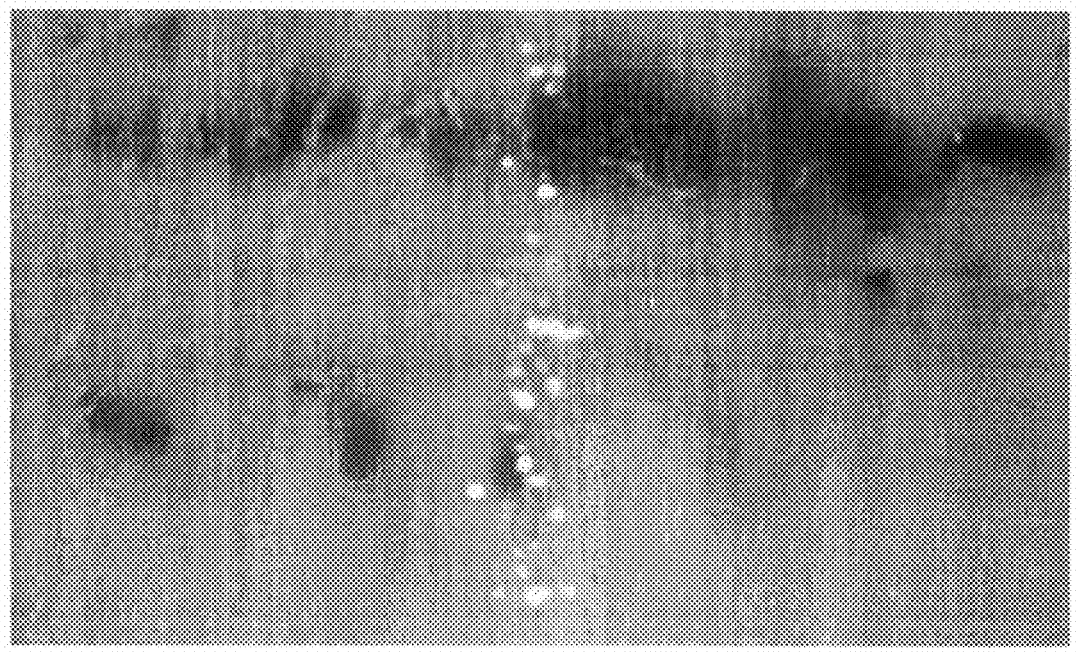
FIG. 5 is a photographic representation of a western blot showing that the production of Enbrel® in CHO cells is about 5 times higher from the codon-modified Enbrel® nucleotide sequence [SEQ ID NO:3] than from the parent or unmodified Enbrel® nucleotide sequence[SEQ ID NO:1].

| SEQUENCE ID NUMBER | SEQUENCE | LENGTH |
|---|---|---|
| SEQ ID NO: 1 | Parent nucleotide sequence encoding Enbrel ® | 1470 nts |
| SEQ ID NO: 2 | Amino acid sequence of Enbrel ® | 489 aa |
| SEQ ID NO: 3 | Codon-modified nucleotide sequence encoding Enbrel ® | 1470 nts |
| SEQ ID NO: 4 | Wild-type nucleotide sequence encoding HPV16E7 | 297 nts |
| SEQ ID NO: 5 | Amino acid sequence of HPV16E7 | 98 aa |
| SEQ ID NO: 6 | Codon-modified nucleotide sequence encoding HPV16E7 | 297 nts |
| SEQ ID NO: 7 | Wild-type nucleotide sequence encoding hGH | 654 nts |
| SEQ ID NO: 8 | Amino acid sequence of hGH | 217 aa |
| SEQ ID NO: 9 | Codon-modified nucleotide sequence encoding hGH | 654 nts |
| SEQ ID NO: 10 | Enbrel ® F1 oligonucleotide | 80 nts |
| SEQ ID NO: 11 | Enbrel ® R1 oligonucleotide | 77 nts |
| SEQ ID NO: 12 | Enbrel ® F2 oligonucleotide | 78 nts |
| SEQ ID NO: 13 | Enbrel ® R2 oligonucleotide | 89 nts |
| SEQ ID NO: 14 | Enbrel ® F3 oligonucleotide | 58 nts |
| SEQ ID NO: 15 | Enbrel ® R3 oligonucleotide | 59 nts |
| SEQ ID NO: 16 | hGH F1 oligonucleotide | 86 nts |
| SEQ ID NO: 17 | hGH R1 oligonucleotide | 70 nts |
| SEQ ID NO: 18 | hGH F2 oligonucleotide | 80 nts |
| SEQ ID NO: 19 | hGH R2 oligonucleotide | 74 nts |
| SEQ ID NO: 20 | hGH F3 oligonucleotide | 65 nts |
| SEQ ID NO: 21 | hGH R3 oligonucleotide | 68 nts |
| SEQ ID NO: 22 | Genomic hGH F1 oligonucleotide | 97 nts |
| SEQ ID NO: 23 | Genomic hGH R1 oligonucleotide | 64 nts |
| SEQ ID NO: 24 | Genomic hGH F2 oligonucleotide | 31 nts |

TABLE A-continued

| SEQUENCE ID NUMBER | SEQUENCE | LENGTH |
|---|---|---|
| SEQ ID NO: 25 | Genomic hGH R2 oligonucleotide | 27 nts |
| SEQ ID NO: 26 | Wild-type genomic sequence encoding hGH | 1679 nts |
| SEQ ID NO: 27 | Amino acid sequence of hGH | 217 aa |
| SEQ ID NO: 28 | Codon-modified nucleotide sequence encoding hGH | 1679 nts |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, frequency, percentage, dimension, size, or amount that varies by as much as 30%, preferably by as much as 20%, and more preferably by as much as 10% to a reference quantity, level, value, frequency, percentage, dimension, size, or amount.

As used herein, the term "cis-acting sequence" or "cis-regulatory region" or similar term shall be taken to mean any sequence of nucleotides which is derived from an expressible genetic sequence wherein the expression of the genetic sequence is regulated, at least in part, by the sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art.

By "expressing the polynucleotide" is meant transcribing the polynucleotide such that mRNA and the encoded protein product are produced.

By "expression vector" is meant any autonomous genetic element capable of directing the synthesis of a protein encoded by the vector. Such expression vectors are known by practitioners in the art.

The term "gene" is used in its broadest context to include both a genomic DNA region corresponding to the gene as well as a cDNA sequence corresponding to exons or a recombinant molecule engineered to encode a functional form of a product.

By "highly expressed genes" is meant genes that express high levels of mRNA, and preferably high level of protein, relative to other genes.

By "isoaccepting transfer RNA" or "iso-tRNA" is meant one or more transfer RNA molecules that differ in their anti-codon nucleotide sequence but are specific for the same amino acid.

By "natural gene" is meant a gene that naturally encodes the protein. However, it is possible that the parent polynucleotide encodes a protein that is not naturally-occurring but has been engineered using recombinant techniques.

The term "5' non-coding region" is used herein in its broadest context to include all nucleotide sequences which are derived from the upstream region of an expressible gene, other than those sequences which encode amino acid residues which comprise the polypeptide product of the gene, wherein 5' non-coding region confers or activates or otherwise facilitates, at least in part, expression of the gene.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The term "operably connected" or "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e. the genes from which it is derived.

The term "polynucleotide" or "nucleic acid" as used herein designates mRNA, RNA, cRNA, cDNA or DNA. The term typically refers to oligonucleotides greater than 30 nucleotides in length.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridise with a target nucleotide sequence. Preferably, the primer contains no mismatches with the template to which it is designed to hybridise but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridise therewith and thereby form a template for synthesis of the extension product of the primer.

By "producing", and like terms such as "production" and "producible", in the context or protein production, is meant production of a protein to a level sufficient to effect a particular function associated with the protein. By contrast, the terms "not producible" and "not substantially producible" as used interchangeably herein refers to (a) no production of a protein, (b) production of a protein to a level that is not sufficient to effect a particular function associated with the protein, (c) production of a protein, which cannot be detected by a monoclonal antibody specific for the protein, or (d) production of a protein, which is less that 1% of the level produced in a wild-type cell that normally produces the protein.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Preferred promoters according to the invention may contain additional copies of one or more specific regulatory elements to further enhance expression in a cell, and/or to alter the timing of expression of a structural gene to which it is operably connected.

By "recombinant polypeptide" is meant a polypeptide made using recombinant techniques, i.e., through the expression of a recombinant or synthetic polynucleotide.

The term "synthetic polynucleotide" as used herein refers to a polynucleotide formed in vitro by the manipulation of a polynucleotide into a form not normally found in nature. For example, the synthetic polynucleotide can be in the form of an expression vector. Generally, such expression vectors include transcriptional and translational regulatory polynucleotide operably linked to the polynucleotide.

The term "synonymous codon" as used herein refers to a codon having a different nucleotide sequence than another codon but encoding the same amino acid as that other codon.

By "translational efficiency" is meant the efficiency of a cell's protein synthesis machinery to incorporate the amino acid encoded by a codon into a nascent polypeptide chain. This efficiency can be evidenced, for example, by the rate at which the cell is able to synthesise the polypeptide from an RNA template comprising the codon, or by the amount of the polypeptide synthesised from such a template.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

2. Abbreviations

HPV: human papillomavirus
PV: papillomavirus
VLP: virus like particle
HGH: human growth hormone gfp: green fluorescent protein gene
GFP: green fluorescent protein
3. Translational Efficiency of Codons in CHO Cells The present invention provides for the first time translational efficiency values for individual synonymous codons in Chinese Hamster Ovary (CHO) cells. These values were determined by transfecting CHO cells with a series of 59 reporter constructs each comprising a gfp gene preceded in frame by an artificial start codon and a tandem repeat of 5 identical codons. This series is described in detail in WO 00/42215 and covers the entire set of synonymous codons that code for amino acids. The fluorescence intensity of the transiently transfected CHO cells was then determined by flow cytometry to provide a measure of GFP produced from each construct. The amount of GFP produced by a CHO cell is sensitive to the intracellular abundance of the iso-tRNA species corresponding to the tandem repeat of identical codons under test and provides, therefore, a direct correlation of a given codon's translational efficiency in the CHO cell. Accordingly, the higher the amount of GFP produced from a given construct in the CHO cell, the higher the translational efficiency will be of the codon which is tandemly repeated in the construct.

TABLE 1 supra presents the relative translational efficiencies of 59 different codons, which were obtained by measuring the mean fluorescence intensities produced by the various constructs in up to 15 different samples of transiently transfected CHO cells. These results reveal that the variation in GFP production levels across the synonymous codons for a single amino acid ranges from about 1 for both glutamine and tyrosine to about 10-fold for glycine, with a median of about 2-fold. They also demonstrate that: (1) for several amino acids having three or more choices of synonymous codon there are (a) codons with translational efficiencies that are at least about 30% higher than the median translational efficiency of the synonymous codons, (b) codons with translational efficiencies that are at least about 30% lower than the median translational efficiency of the synonymous codons, and (c) codons with translational efficiencies intermediate those of (a) and (b); and (2) for several amino acids having two choices of synonymous codon there is (i) one codon with a translational efficiency that is at least about 10% higher than the translational efficiency of the other synonymous codon; and (ii) one codon with a translational efficiency that is at least about 10% lower than the translational efficiency of the other synonymous codon. In accordance with the present invention, codons that fall into categories 1(a) and 2(i) are deemed to be 'high' efficiency codons, codons that fall into category 2(c) are deemed to be 'intermediate' or 'moderate' efficiency codons, and codons that fall into categories 1(b) and 2(ii) are deemed to be 'low' efficiency codons, as set forth in TABLE 4 supra. Comparison of the translational efficiencies so classified with the translational efficiencies derived from codon usage frequency values for mammalian cells in general as determined by Seed (see U.S. Pat. Nos. 5,786,464 and 5,795,737) reveals several differences in the ranking of translational efficiencies. For convenience, these differences are highlighted in TABLE 7, wherein Seed preferred codons are highlighted with bold print, Seed less preferred codons are highlighted with italics print, and Seed non codons are highlighted with underlining

TABLE 7

| Amino Acid | Preferential codon usage as predicted by Seed for mammalian cells in general | | | Experimentally determined translational efficiency of codons in CHO-cells | | |
|---|---|---|---|---|---|---|
| | Preferred | Less Preferred | Non-preferred | High | Intermediate | Low |
| Ala | GCC | | GCG, GCT, GCA | GCA | GCG, GCT | GCC |
| Arg | CGC | | CGA, CGT, AGA, AGG, CGG | | AGA, CGG, CGA, CGT, AGG | CGC |
| Asn | AAC | | AAT | | AAC, AAT | |
| Asp | GAC | | GAT | GAT | | GAC |
| Cys | TGC | | TGT | TGC | | TGT |
| Glu | | | GAA, GAG | GAG GAA | | GAG |
| Gln | CAG | | CAA | | CAA, CAG | |
| Gly | GGC | GGG | GGT, GGA | GGA | | GGC, GGG, GGT |
| His | CAC | | CAT | | CAC, CAT | |
| Ile | ATC | ATT | ATA | | ATT, ATC, ATA | |
| Leu | CTG | CTC | TTA, CTA, CTT, TTG | TTG | CTC, CTA, CTG | TTA, CTT |
| Lys | AAG | | AAA | AAG | | AAA |
| Phe | TTC | | TTT | | TTT, TTC | |
| Pro | CCC | | CCG, CCA, CCT | | CCC, CCA, CCG | CCT |
| Ser | AGC | TCC | TCG, AGT, TCA, TCT | | AGC, TCT, AGT, TCA, TCG, TCC | |
| Thr | ACC | | ACG, ACA, ACT | | ACA, ACG, ACT | ACC |
| Tyr | TAC | | TAT | | TAC, TAT | |
| Val | GTG | GTC | GTA, GTT | GTA, GTT | GTA, GTC, GTG | |

As will be apparent from the above table:
(1) several codons, which have been deemed by Seed to be preferred codons (Ala$^{GCC}$, Arg$^{CGC}$, Asp$^{GAC}$, Gly$^{GGC}$ and Thr$^{ACC}$), have in fact much lower translational efficiencies than other synonymous codons;
(2) several codons, which have been deemed by Seed to be non preferred codons (Ala$^{GCA}$, Asp$^{GAT}$, Glu$^{GAA}$, Gly$^{GGA}$ and Leu$^{TTG}$), have in fact much higher translational efficiencies than other synonymous codons;
(3) several codons, which have been deemed by Seed to be preferred (Asn$^{AAC}$, Gln$^{CAG}$, His$^{CAC}$, Ile$^{ATC}$, Leu$^{CTG}$, Phe$^{TTC}$, Pro$^{CCC}$, Ser$^{AGC}$, Tyr$^{TAC}$ and Val$^{GTG}$), or non preferred (Ala$^{GCG}$, Ala$^{GCT}$, Arg$^{AGA}$, Arg$^{CGG}$, Arg$^{CGA}$, Arg$^{CGT}$, Arg$^{AGG}$, Asn$^{AAT}$, Gln$^{CAA}$, His$^{CAT}$, Ile$^{ATA}$, Leu$^{CTA}$, Phe$^{TTT}$, Pro$^{CCA}$, Pro$^{CCG}$, Pro$^{CCT}$, Ser$^{TCT}$, Ser$^{AGT}$, Ser$^{TCG}$, Ser$^{TCA}$, Thr$^{ACA}$, Thr$^{ACG}$, Thr$^{ACT}$, Tyr$^{TAT}$, Val GTA and Val$^{GTT}$) have moderate translational efficiencies; and
(4) codon Leu$^{CTC}$, which has been deemed by Seed to be less preferred codons, is in fact a highly translationally efficient codon.

Accordingly, the present invention enables for the first time the modulation of protein production from a parent polynucleotide in a CHO cell by replacing one or more codons of that polynucleotide with synonymous codons that have higher or lower translational efficiencies than the codons they replace. In one embodiment, therefore, the present invention embraces a method of constructing a synthetic polynucleotide from which a protein is producible at a higher level in a CHO cell than from a parent polynucleotide encoding the same protein. This method comprises selecting from TABLE 1 a codon (often referred to herein as a "first codon") of the parent polynucleotide for replacement with a synonymous codon, wherein the synonymous codon is selected on the basis that it exhibits a higher translational efficiency in the CHO cell than the first codon.

When selecting the synonymous codon, it is preferred that it has a translational efficiency in the CHO cell that is at least about 110%, suitably at least about 120%, preferably at least about 130%, more preferably at least about 140%, even more preferably at least about 150%, even more preferably at least about 160%, even more preferably at least about 170%, even more preferably at least about 180%, even more preferably at least about 190%, even more preferably at least about 200%, even more preferably at least about 250%, even more preferably at least about 300%, even more preferably at least about 350%, even more preferably at least about 400%, even more preferably at least about 450%, even more preferably at least about 500%, even more preferably at least about 550%, even more preferably at least about 600%, even more preferably at least about 650%, and still even more preferably at least about 700% of the translational efficiency of the first codon it replaces. In the case of two or more synonymous codons having similar translational efficiencies, it will be appreciated that any one of these codons can be used to replace the first codon.

In another embodiment, the synonymous codon and the first codon are both selected from TABLE 4 supra on the basis that: (a) if the first codon is classified as a 'low' translationally efficient codon, then the synonymous codon is selected from a 'high' or 'intermediate' translationally efficient codon; or (b) if the first codon is classified as an 'intermediate' translationally efficient codon, then the synonymous codon is selected from a 'high' translationally efficient codon. For convenience, the relevant selections are presented in TABLE 5 supra. Once selected, the first codon(s) is/are replaced with the synonymous codon(s) to construct the synthetic polynucleotide from which the protein of interest is produced at a higher level than from the parent polynucleotide.

Thus, in accordance with the present invention, a parent polynucleotide can be modified with synonymous codons such that translation of a protein in a CHO from the polynucleotide so modified (synthetic polynucleotide) is higher than from the parent polynucleotide. Generally, the difference in level of protein produced in the CHO cell from a synthetic polynucleotide relative to that produced from a parent polynucleotide depends on the number of first codons that are replaced by synonymous codons, and on the difference in translational efficiencies between the first codons and the synonymous codons in the CHO cell. Put another way, the fewer such replacements, and/or the smaller the difference in translational efficiencies between the synonymous and first codons, the smaller the difference will be in protein production between the synthetic polynucleotide and parent polynucleotide. Conversely, the more such replacements, and/or the greater the difference in translational efficiencies between the synonymous and first codons, the greater the difference will be in protein production between the synthetic polynucleotide and parent polynucleotide.

It is preferable but not necessary to replace all the codons of the parent polynucleotide with synonymous codons having higher translational efficiencies in the CHO cells than the first codons. Increased expression can be accomplished even with partial replacement. Typically, the replacement step affects at least about 5%, 10%, 15%, 20%, 25%, 30%, more preferably at least about 35%, 40%, 50%, 60%, 70% or more of the first codons of the parent polynucleotide. Suitably, the number of, and difference in translational efficiency between, the first codons and the synonymous codons are selected such that the protein of interest is produced from the synthetic polynucleotide in the CHO cell at a level which is at least about 110%, suitably at least about 150%, preferably at least about 200%, more preferably at least about 250%, even more preferably at least about 300%, even more preferably at least about 350%, even more preferably at least about 400%, even more preferably at least about 450%, even more preferably at least about 500%, and still even more preferably at least about 1000%, of the level at which the protein is produced from the parent polynucleotide in the CHO cell.

Generally, if a parent polynucleotide has a choice of low and intermediate translationally efficient codons, it is preferable in the first instance to replace some, or more preferably all, of the low translationally efficient codons with synonymous codons having intermediate, or preferably high, translational efficiencies. Typically, replacement of low with intermediate or high translationally efficient codons results in a substantial increase in production of the polypeptide from the synthetic polynucleotide so constructed. However, it is also preferable to replace some, or preferably all, of the intermediate translationally efficient codons with high translationally efficient codons for optimised production of the polypeptide.

In another embodiment, the present invention contemplates a method of constructing a synthetic polynucleotide from which a protein is producible at a lower level in a CHO cell than from a parent polynucleotide encoding the same protein. This may be desirable when high level production of the protein has a deleterious effect on the CHO cell. Alternatively, or in addition, the protein-encoding polynucleotide can be modified to introduce a local decrease in translational efficiency to assist in protein folding during translation. In this regard, it is proposed that protein folding may be enhanced when the codon alteration introduces a translational pause in a portion of the protein-encoding polynucleotide. In this embodiment, therefore, the method comprises selecting from TABLE 1 a codon of the parent polynucleotide for replacement with a synonymous codon, wherein the synonymous codon is selected on the basis that it exhibits a lower translational efficiency in the CHO cell than the first codon. It is preferred that the selected synonymous codon has a translational efficiency in the CHO cell that is less than about 90%, suitably less than about 80%, preferably less than about 70%, more preferably less than about 60%, even more preferably less than about 50%, even more preferably less than about 45%, even more preferably less than about 40%, even more preferably less than about 35%, even more preferably less than about 30%, even more preferably less than about 25%, even more preferably less than about 20%, even more preferably less than about 15%, even more preferably less than about 10%, and still even more preferably less than about 5% of the translational efficiency of the codon it replaces.

In another embodiment, the synonymous codon and the first codon are selected from TABLE 4 supra on the basis that: (a) if the first codon is classified as a 'high' translationally efficient codon, then the synonymous codon is selected from an 'intermediate' or 'low' translationally efficient codon; or (b) if the first codon is classified as an 'intermediate' translationally efficient codon, then the synonymous codon is selected from a 'low' translationally efficient codon. For convenience, the relevant selections are presented in TABLE 6 supra. Once selected, the first codon(s) is/are replaced with the synonymous codon(s) to construct a synthetic polynucleotide from which the protein of interest is produced at a lower level than from the parent polynucleotide.

4. Construction and Expression of Synthetic Polynucleotides

Replacement of one codon for another can be achieved using standard methods known in the art. For example codon modification of a parent polynucleotide can be effected using several known mutagenesis techniques including, for example, oligonucleotide-directed mutagenesis, mutagenesis with degenerate oligonucleotides, and region-specific mutagenesis. Exemplary in vitro mutagenesis techniques are described for example in U.S. Pat. Nos. 4,184,917, 4,321,365 and 4,351,901 or in the relevant sections of Ausubel, et al. (CURRENT PROTOCOLS IN MOLECULAR BIOLOGY, John Wiley & Sons, Inc. 1997) and of Sambrook, et al., (MOLECULAR CLONING. A LABORATORY MANUAL, Cold Spring Harbor Press, 1989). Instead of in vitro mutagenesis, the synthetic polynucleotide can be synthesised de novo using readily available machinery as described, for example, in U.S. Pat. No. 4,293,652. However, it should be noted that the present invention is not dependent on, and not directed to, any one particular technique for constructing the synthetic polynucleotide.

The parent polynucleotide is preferably a natural gene. However, it is possible that the parent polynucleotide that is not naturally-occurring but has been engineered using recombinant techniques. Parent polynucleotides can be obtained from any suitable source, such as from eukaryotic or prokaryotic organisms, including but not limited to mammals or other animals, and pathogenic organisms such as yeasts, bacteria, protozoa and viruses.

The invention also contemplates synthetic polynucleotides encoding one or more desired portions of a protein of interest. In this regard, it is preferable that the synthetic polynucleotide encodes at least one functional domain of the protein, which is preferably at least about 10, more preferably at least about 20, even more preferably at least about 50, even more preferably at least about 100, even more preferably at least about 150, and still more preferably at least about 500 contiguous amino acid residues of the protein.

The invention further contemplates a synthetic construct (or expression vector), comprising a synthetic polynucleotide of the invention, which is operably linked to a regulatory polynucleotide. The regulatory polynucleotide suitably comprises transcriptional and/or translational control sequences, which will be compatible for expression in CHO cells. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the CHO cell or may be derived from an alternative source, where the region is functional in the CHO cell. Exemplary promoters which could be used for expression in CHO cells include mammalian promoters such as the metallothionein promoter, which can be induced in response to heavy metals such as cadmium, and the β-actin promoter. Viral promoters such as the SV40 large T antigen promoter, human cytomegalovirus (CMV) immediate early (IE) promoter, rous sarcoma virus LTR promoter, adenovirus promoter, or a HPV promoter, particularly the HPV upstream regulatory region (URR) may also be used. All these promoters are well described and readily available in the art.

The synthetic construct of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by the presence of homology to the canonical form 5' AATAAA-3' although variations are not uncommon. The 3' non-translated regulatory DNA sequence preferably includes from about 50 to 1,000 nucleotide base pairs and may contain transcriptional and translational termination sequences in addition to a polyadenylation signal and any other regulatory signals capable of effecting mRNA processing or gene expression.

In a preferred embodiment, the synthetic construct further contains a selectable marker gene to allow the selection of transfected CHO cells. Selection genes are well known in the art and will be compatible for expression in CHO cells.

In another preferred embodiment, the synthetic construct includes a fusion partner (typically provided by an expression vector) so that the recombinant polypeptide is producible as a fusion polypeptide with the fusion partner. The main advantage of fusion partners is that they assist identification and/or purification of the fusion polypeptide. In order to express the fusion polypeptide, it is necessary to ligate the synthetic polynucleotide in reading frame with a polynucleotide encoding the fusion partner. Well known examples of fusion partners include, but are not limited to, glutathione-S-transferase (GST), Fc potion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system. In a preferred embodiment, the recombinant polynucleotide is expressed in the commercial vector pFLAG as described more fully hereinafter. Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation. Fusion partners according to the invention also include within their scope "epitope tags", which are usually short peptide sequences for which a specific antibody is available. Well known examples of epitope tags for which specific monoclonal antibodies are readily available include c-Myc, influenza virus, haemagglutinin and FLAG tags.

The synthetic constructs of the invention can be introduced into a CHO cell using any suitable transfection including, for example, electroporation, microparticle bombardment, liposomes, viral or phage infection and the like. Such methods are well known to those of skill in the art.

It will be understood, however, that expression of protein-encoding polynucleotides in heterologous systems is now well known, and the present invention is not directed to or dependent on any particular vector or technique. Rather, synthetic polynucleotides prepared with the modifications set forth herein may be used to transfect a CHO cell in any suitable manner in conjunction with any suitable synthetic construct or vector, and the synthetic polynucleotides may be expressed with known promoters in any conventional manner.

Recombinant proteins of the invention may be produced by culturing a CHO cell transfected with the synthetic construct of the invention and the conditions appropriate for expression of polynucleotides in CHO cells are well known in the art. The recombinant protein so produced may be purified by a person skilled in the art using standard protocols as for example described in Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6.

5. Protein Production in CHO Cells by Expression of Isoaccepting Transfer RNA-encoding Polynucleotides The invention also features a method of modifying a CHO cell so that a protein is producible at a higher level from a first polynucleotide encoding the protein. This method comprises selecting a codon of the first polynucleotide, whose translational efficiency limits the production of the protein and whose corresponding isoaccepting transfer RNA (iso-tRNA) is not produced in relatively high abundance in the CHO cell. A second polynucleotide is then introduced into the CHO cell, which is capable of producing that iso-tRNA to a level sufficient for enhancing the production of the protein from the first polynucleotide.

In practice, an iso-tRNA is supplied to the CHO cell by the second polynucleotide when an iso-tRNA is in relatively low abundance in the CHO cell and when the first polynucleotide comprises codons specific for that iso-tRNA. Broadly speaking, the supplied iso-tRNAs may be specific for codons that have 'low' or 'intermediate' translational efficiencies in CHO cells, which are set forth in TABLE 4 supra and which may be selected from the group consisting of $Ala^{GCC}$, $Ala^{GCT}$, $Ala^{GCG}$, $Arg^{AGA}$, $Arg^{CGG}$, $Arg^{CGA}$, $Arg^{CGT}$, $Arg^{AGG}$, $Arg^{CGC}$, $Asn^{AAC}$, $Asn^{AAT}$, $Asp^{GAC}$, $Cys^{TGT}$, $Glu^{GAG}$, $Gln^{CAA}$, $Gln^{CAG}$, $Gly^{GGC}$, $Gly^{GGG}$, $Gly^{GGT}$, $His^{CAC}$, $His^{CAT}$, $Ile^{ATT}$, $Ile^{ATC}$, $Ile^{ATA}$, $Leu^{CTA}$, $Leu^{CTG}$, $Leu^{TTA}$, $Leu^{CTT}$, $Lys^{AAA}$, $Phe^{TTT}$, $Phe^{TTC}$, $Pro^{CCC}$, $Pro^{CCA}$, $Pro^{CCG}$, $Pro^{CCT}$, $Ser^{AGC}$, $Ser^{TCT}$, $Ser^{AGT}$, $Ser^{TCG}$, $Ser^{TCA}$, $Ser^{TCC}$, $Thr^{ACA}$, $Thr^{ACG}$, $Thr^{ACT}$, $Thr^{ACC}$, $Tyr^{TAC}$, $Tyr^{TAT}$, $Val^{GTA}$, $Val^{GTT}$, $Val^{GTC}$ and $Val^{GTG}$. In a preferred embodiment, the supplied iso-tRNAs are specific for codons that have 'low' translational efficiencies in CHO cells, which are set forth in TABLE 4 and which may be selected from the group consisting of $Ala^{GCC}$, $Arg^{CGC}$, $Asp^{GAC}$, $Cys^{TGT}$, $Glu^{GAG}$, $Gly^{GGC}$, $Gly^{GGG}$, $Gly^{GGT}$, $Leu^{TTA}$, $Leu^{CTT}$, $Lys^{AAA}$ and $Thr^{ACC}$.

6. Enhancing Production of Virus Particles in CHO Cells

The invention also provides a method of producing virus particles in CHO cells. The virus particles will typically comprise at least one protein that is necessary for virus assembly, wherein the or each protein is not producible in the cell from a parent polynucleotide at a level sufficient to permit productive virus assembly therein, which are referred to hereafter as assembly-limiting proteins. This method comprises selecting from TABLES 1 or 2 supra a first codon of the parent polynucleotide for replacement with a synonymous codon, wherein the synonymous codon is selected on the basis that it exhibits a higher translational efficiency in the CHO cell than the first codon. Suitable selections can be made according to Section 3. The first codon is then replaced with the synonymous codon to construct the synthetic polynucleotide, as for example described in Section 4. The synthetic polynucleotide so produced is operably linked to a regulatory polynucleotide and is then introduced into the CHO cell whereby the assembly-limiting protein(s) is produced in the cell in the presence of other viral proteins required for assembly of the virus particle to thereby produce the virus particle.

The assembly-limiting protein is preferably a viral capsid protein or capsomer. Suitable viral capsid proteins include, but are not restricted to, the L1 and L2 proteins of papillomavirus, VP1-3 of polyomavirus, VP1-6 of blue tongue virus, and the capsid proteins of adenovirus.

The other viral proteins required for assembly of the virus particle in the CHO cell can be produced from one or more other polynucleotides which suitably contain the rest of the viral genome. Preferably, when the assembly-limiting protein(s) is selected from L1 or L2 of papillomavirus, the other polynucleotide(s) preferably comprises the papillomavirus genome without the L1- and/or L2-encoding sequences.

In another embodiment, there is provided a method for producing a virus particle in a CHO cell wherein the virus particle comprises at least one assembly-limiting protein as mentioned above, which is produced from a parent polynucleotide. In this embodiment, at least one codon of the parent polynucleotide is rate-limiting for the production of the assembly-limiting protein(s) and is hereafter referred to as a rate-limiting codon. The method includes introducing into the CHO cell a polynucleotide from which an iso-tRNA is expressible, which is specific for the rate-limiting codon(s). Suitable rate-limiting codons may be selected according to Section 5.

The invention also provides virus particles made by any one of the above methods, as well as CHO cells containing therein the synthetic polynucleotides of the invention, or alternatively, CHO cells produced from the methods of the invention.

5. Pharmaceutical Compositions

A further feature of the invention is the use of the polypeptides produced according to Sections 4 and 5 as actives in pharmaceutical compositions for treating, preventing or alleviating the symptoms of conditions that are ameliorable using such polypeptides. Suitably, the pharmaceutical composition comprises a pharmaceutically acceptable carrier. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Any suitable route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is therapeutically- or prophylactically-effective to alleviate patients from symptoms related to the condition(s), or in amounts sufficient to protect patients from developing symptoms related to the condition(s). The dose administered to a patient, in the context of the present invention, should be sufficient to achieve a beneficial response in a patient over time such as the therapeutic or prophylactic effects mentioned above. The quantity of the polypeptide(s) to be administered may depend on the subject to be treated inclusive of the age, sex, weight and general health condition thereof. In this regard, precise amounts of the polypeptide(s) for administration will depend on the judgement of the practitioner. In determining the effective amount of the polypeptide to be administered in the treatment or prophylaxis of the condition(s), the physician may evaluate progression of the condition(s). In any event, suitable dosages of the polypeptides prepared according to the invention may be readily determined by those of skill in the art. Such dosages may be in the order of nanograms to milligrams of the polypeptides.

In order that the invention may be readily understood and put into practical effect, particular preferred embodiments will now be described by way of the following non-limiting examples.

EXAMPLES

Example 1

Construction of Codon Modified Enbrel®-encoding Polynucleotide for Enhanced Expression in CHO Cells Enbrel® (also known as etanercept) is a recombinant fusion protein consisting of two soluble TNF receptors joined by the Fc fragment of a human IgG1 molecule, whose amino acid sequence is set forth in SEQ ID NO:2. The unmodified gene sequence is shown in SEQ ID NO:1 and several codons (CTG encoding Leu10 and Leu14; GAG encoding Glu15 and Glu35; GGG encoding Gly37; GGC encoding Gly60; AAA encoding Lys56 and Lys64; CAT encoding His62; TTC encoding Phe66; and ACC encoding Thr68 and Thr70) were identified in this sequence, which have low translational efficiencies as set forth in TABLES 1 and 2. Synonymous codons (Leu$^{CTC}$, Glu$^{GAA}$, Gly$^{GGA}$, Lys$^{AAG}$, His$^{CAC}$, Phe$^{TTT}$ and Thr$^{ACA}$) with higher translational efficiencies were then chosen for replacing the low translationally efficient codons. For convenience, these replacements are shown in FIG. 1, which depicts a comparison of the modified and unmodified Enbrel® gene sequences.

Cassette mutagenesis was then used to replace the low translational efficient codons of the unmodified gene sequence with the higher translationally efficient codons. Briefly, 100 pmol of the following oligonucleotides were made up to 40 µL total volume using sterile, nuclease free water.

[SEQ ID NO: 10]
(a) F1 (5'-CATGGCGGCCCGTCGCCGTCTGGGCCGCGCTCGCCG
TCGGACTC GAACTCTGGGCTGCGGCACGCCTTGCCCGCCCAG
GT-3'); and

[SEQ ID NO: 11]
R1 (5'-GGGCGGGCAAGGCGTGCGCCGCAGCCCAGAGATCGA
GTCCGACGGC GAAGCGCGGCCCCAGACGGCGCGACGGGC
GC-3'); or

[SEQ ID NO: 12]
(b) F2 (5'-GGCATTTACACCCTACGCCCCGGAACGCGGAAGCAC
ATGCCGGC TCAGAGAATACTATGACAGCTCAGATGTGCTG
CA-3'); and

[SEQ ID NO: 13]
R2 (5'-GCACATCTGAGCTGTCTGGTCATAGTATTCTCTGAG
CCGGCATGTGCTTTCCGGGTTTCCGGGTCCGGGGCGTAGGGTG
TAAATGCCACGT-3'); or

[SEQ ID NO: 14]
(c) F3 (5'-GCAAGTGCTCGCCGGGACAACACGCAAAGGTCTTTT
TGTACAAAG ACATCGGACACCGT-3'); and

[SEQ ID NO: 15]
R3 (5'-GTGTCCGATGTCTTTGTACAAAAGACCTTTTGCGTG
TTGTCCCGGCGAGCACTTGCTGCA-3').

Individual oligonucleotide pairs were annealed by heating at 100° C. for 2 mins, incubating at 37° C. for 2 hours, and cooling to room temperature. The annealed oligonucleotides were then ligated, gel purified and ligated into an Enbrel® gene-containing pUC19 vector digested with NcoI/DraIII. The modified and unmodified Enbrel® genes were then removed from pUC19 by digesting with KpnI and HincII and ligated into KpnI/EcoRV digested pCDNA3, for expression in CHO cells.

Example 2

Construction of Codon Modified HPV16E7-encoding Polynucleotide for Enhanced Expression in CHO Cells The wild-type coding sequence of HPV16E7 is shown in SEQ ID NO:4 and several codons (CAT encoding His2, His9 and His51; CCT encoding Pro6; CCA encoding Pro17, and Pro98; CCG encoding Pro47; TTG encoding Leu8, Leu15, Leu67 and Leu79; TTA encoding Leu13, Leu28 and Leu83; CTT encoding Leu65; CTG encoding Leu82; CTA encoding Leu87; GAG encoding Glu18, Glu26, Glu33, Glu34 and Glu35; ACT encoding Thr20 and Thr78; ACC encoding Thr56; TGT encoding Cys24, Cys58, Cys61 and Cys94; AAT encoding Asn29 and Asn53; GAC encoding Asp30, Asp48, Asp62, Asp75 and Asp81; TCA encoding Ser32; GCT encoding Ala42; GCC encoding Ala50; GGC encoding Gly85; and AAA encoding Lys97) were identified in this sequence, which have low translational efficiencies as set forth in TABLES 1 and 4. Synonymous codons (His$^{CAC}$, Pro$^{CCC}$, Leu$^{CTC}$, Glu$^{GAA}$, Cys$^{TGC}$, Asn$^{AAC}$, Asp$^{GAT}$, Ser$^{TCT}$, Ala$^{GCA}$, Thr$^{ACA}$, Gly$^{GGA}$ and Lys$^{AAG}$) with higher translational efficiencies were then chosen for replacing the low translationally efficient codons. For convenience, these replacements are shown in FIG. 2, which depicts a comparison of the modified and wild-type HPV16E7 coding sequences.

The modified HPV16E7 coding sequence was constructed commercially (Operon) and was ligated directionally into the BamHI and EcoRI sites of pCDNA3 for expression in CHO cells.

Example 3

Construction of Codon Modified Human Growth Hormone cDNA for Enhanced Expression in CHO Cells The wild-type coding sequence of human growth hormone (hGH) is shown in SEQ ID NO:7 and several codons (GCT encoding Ala2, Ala12 and Ala29; GCC encoding Ala26, Ala43, Ala50 and Ala60; ACA encoding Thr3; ACC encoding Thr29 and Thr53; GGC encoding Gly4, Gly14 and Gly24; TCC encoding Ser5, Ser8 and Ser33; AGT encoding Ser25; TCA encoding Ser69; CTG encoding Leu9, Leu11, Leu15, Leu18, Leu46 and Leu49; CTT encoding Leu21; TTA encoding Leu32; GAG encoding Glu23 and Glu56; TTC encoding Phe27 and Phe70; CCA encoding Pro28 and Pro63; CCT encoding Pro35; AGG encoding Arg34; CGC encoding Arg42; GAC encoding Asp37; and CAT encoding His44) were identified in this sequence, which have low translational efficiencies as set forth in TABLES 1 and 2. Synonymous codons (Ala$^{GCA}$, Gly$^{GGA}$, Ser$^{TCT}$, Leu$^{CTC}$, Glu$^{GAA}$, Phe$^{TTT}$, Pro$^{CCC}$, Thr$^{ACA}$, Arg$^{AGA}$, His$^{CAC}$ and Asp$^{GAT}$) with higher translational efficiencies were then chosen for replacing the low translationally efficient codons. For convenience, these replacements are shown in FIG. 3, which depicts a comparison of the modified and wild-type hGH coding sequences.

Cassette mutagenesis was then used to replace the low translational efficient codons of the wild-type coding sequence with the higher translationally efficient codons as described for Example 1, except that the following oligonucleotides were use in place of primers used for that example.

[SEQ ID NO: 16]
(a) F1 (5'-GATCCACCATGGCAACAGGATCTCGGACGTCTCTC
    CTCCTCGCAT TTGGACTCCTCTGCCTCCCCTGGCTCCAAGA
    AGAAGGAAGC-3');
and

[SEQ ID NO: 17]
R1 (5'-TTCTTGGAGCCAGGGGAGGCAGAGGAGTCCAAATGC
    GAGGAGGAGAGACGTCCGAGATCCTGTTGCCATG-3');
or

[SEQ ID NO: 18]
(b) F2 (5'-GCATTTCCCACAATTCCCTCCCCTCTCTAGACCCT
    TTGATAACG CAATGCTCGGGGCACACCGTCTCCACCAGCTC
    GCA-3'); and

[SEQ ID NO: 19]
R2 (5'-TGGTGGAGACGGTGTGCCCGGAGCATTGCGTTATCA
    AAGGGTCTAGAGAGGGGAATTGTGGGAAATGCGCTTCC-3');
or

[SEQ ID NO: 20]
(c) F3 (5'-TTTGACACATACCAGGAATTTGAAGAAGCATATAT
    CCCCAAGGA ACAGAAGTATTCTTTTCTGCA-3'); and

[SEQ ID NO: 21]
R3 (5'-GAAAAGAATACTTCTGTTCCTTGGGGATATATGCT
    TCTTCAAATTCCTGGTATGTGTCAAATGCGAGC-3').

The annealed oligonucleotides were then ligated, gel purified and ligated into an hGH gene digested with BamHI and DraII. The modified and wild-type hGH coding sequences were then ligated into pCDNA3 for expression in CHO cells.

Example 4

Construction of Codon Modified Human Growth Hormone Genomic DNA for Enhanced Expression in CHO Cells A genomic hGH clone was subcloned into pCDNA3 and the BamHI/SacI fragment of this subclone was further subcloned into pUC18. The resulting pUC18 subclone was used as a template for PCR amplification, using the following primers:

[SEQ ID NO: 22]
(a) F1 (5'-CCGGGCCAACATGGCTACAGGATCTCGGACGTCTC
    TCCTCCTCGCA TTTGGACTCCTCTGCCTCCCCTGGCTCCAA
    GAAGGAAGCGCATTTCCCACA-3'); and

[SEQ ID NO: 23]
(b) R1 (5'-GCGCGGCCAGCTGGTGGAGACGGTGTGCCCGGAGC
    ATTGCGTTTGTC AAAGGGTCTAGAGAGGGG-3').

The amplified product was cloned into the BamHI/PvuII site of the above pUC18 subclone and the resulting modified clone was used as a template for a second PCR amplification, using the following primers:

[SEQ ID NO: 24]
(c) F2 (5'-CAGCTGGCCTTTGACACATACCAGGAAT
    TTG-3'); and

[SEQ ID NO: 25]
(d) R2 (5'-CTTCGGGAAAAACCCTGAGCTCCTT
    AG-3').

The amplified product so obtained was ligated into the PvuII/SacI site of the modified clone and the BamHI/SacI fragment of the resulting second modified clone was then subcloned back into the original hGH pCDNA3 clone.

The wild-type genomic sequence of the hGH gene is shown in SEQ ID NO:26 and various codons within its coding sequence (GGC encoding Gly4, Gly14 and Gly24; TCC encoding Ser5, Ser8 and Ser33; AGT encoding Ser25; CTG encoding Leu9, Leu11, Leu15, Leu18 and Leu46; CTT encoding Leu21; TTA encoding Leu32; GCT encoding Ala12 and Ala39; GCC encoding Ala26 and Ala43; GAG encoding Glu23 and Glu56; TTC encoding Phe27; CCA encoding Pro28; CCT encoding Pro35; ACC encoding Thr29 and Thr53; GAC encoding Asp37; AGG encoding Arg34; CGC encoding Arg42; and CAT encoding His44) were identified as having low translational efficiencies as set forth in TABLES 1 and 2. Synonymous codons (Gly$^{GGA}$, Ser$^{TCT}$, Leu$^{CTC}$, Ala$^{GCA}$, Glu$^{GAA}$, Ser$^{AGT}$, Phe$^{TTT}$, Pro$^{CCC}$, Thr$^{ACA}$, Arg$^{AGA}$, Asp$^{GAT}$, Arg$^{CGG}$ and His$^{CAC}$) with higher translational efficiencies were then chosen for replacing the low translationally efficient codons. The nucleotide sequence of the modified hGH genomic sequence is presented in SEQ ID NO: 28. For convenience, these replacements are shown in FIG. 4, which depicts a comparison of the modified and wild-type hGH genomic sequences.

Example 5

Transient Transfections of CHO Cells with Codon Modified Enbrel® Construct & Western Blotting Chinese hamster ovary cells were cultivated in DMEM/F12 medium (Invitrogen) supplemented with 10% foetal calf serum and 1% Penicillin-Streptomycin-Glutamine solution (Gibco BRL). Cells were transfected using Lipofectamine Plus (Invitrogen). Cells were seeded in T25 flasks 16 h prior to transfection. Plasmid DNA, 4 µg of either the unmodified Enbrel® construct or codon modified Enbrel® construct, were diluted in 750 µL OptiMEM I™ medium (Invitrogen), mixed with 20 µL PlusReagent (Invitrogen) and incubated for 30 min at RT prior to addition of 750 µL OptiMEM I™ medium containing 30 µL Lipofectamine reagent (Invitrogen) and incubation for 30 min at RT. The cell monolayer was washed once with OptiMEM I medium and incubated with 5 mL OptiMEM I™ medium and the transfection mixture overnight, before replacing with 5 mL reduced growth medium (DMEM/F12, 2% foetal calf serum) and cultivated for another 24 hours prior to harvesting. 5 mL cell culture supernatant was harvested. Samples were then concentrated to 100 µL using 50 000 MWCO spin filters (Amicon). Samples were stored at −20° C.

After addition of 5× sample buffer to 20 µL of sample, samples were subjected to SDS-PAGE on 7.5% gels, 150 V for 1 hour. Proteins were electroblotted onto PVDF membrane (Amersham) for 2 hours at 125 mA. After blocking with 5% skim milk powder in PBS/0.5% Tween 20, membranes were probed by addition of 4 µg/mL (1:250) antibodies specific to human IgG Fc region (mouse monoclonal (HP6017), Santa Cruz Biotechnology Inc.). Proteins were visualised using a peroxidase-coupled secondary antibody (mouse anti-human IgG, diluted 1:1000), and a chemiluminescent detection system, exposed to film and developed.

The results presented in FIG. 5 show that the codon modified Enbrel® construct produces about 5 times more Enbrel® than the unmodified Enbrel® construct.

Example 6

Transient Transfections of CHO Cells with Codon Modified HPV16E7 Construct & Western Blotting Chinese hamster ovary cells were cultivated in DMEM/F12 medium (Invitrogen) supplemented with 10% foetal calf serum and 1% Penicillin-Streptomycin-Glutamine solution (Gibco BRL). Cells were transfected using Lipofectamine Plus (Invitrogen). Cells were seeded in T25 flasks 16 h prior to transfection. Plasmid DNA, 4 µg of either HPV 16 E7 wild type or HPV 16 E7 CHO modified were diluted in 750 µL OptiMEM I™ medium (Invitrogen), mixed with 20 µL PlusReagent™ (Invitrogen) and incubated for 30 min at RT prior to addition of 750 µL OptiMEM I™ medium containing 30 µL Lipofectamine reagent (Invitrogen) and incubation for 30 min at RT. The cell monolayer was washed once with OptiMEM I™ medium, incubated with 5 mL OptiMEM I™ medium and the transfection mixture overnight, before replacing with 5 mL growth medium (DMEM/F12, 10% foetal calf serum,) and cultivated another 24 hours prior to harvesting. Cells were harvested and pelleted, then resuspended in 0.1 mL lysis buffer (0.1% NP-40, 2 µg/mL aprotinin, 5 mg/mL DTT, 1 µg/mL leupeptin, 2 mM PMSF), sonicated and stored at −20° C.

After addition of 5× sample buffer to 30 µL of sample, samples were heated to 100° C., 3 mins, and then subjected to SDS-PAGE on 12% gels, 150 V for 1 hour. Proteins were electroblotted onto PVDF membrane (Amersham) for 2 hours at 125 mA. After blocking with 5% skim milk powder in PBS/0.5% Tween 20, membranes were probed by addition of anti-HPV 16 E7 (Santa Cruz Biotech, Santa Cruz, Calif.) diluted 1:1000. Proteins were visualised by a peroxidase-coupled secondary antibody (goat anti-mouse IgG, diluted 1:1000), and a chemiluminescent detection system, exposed to film, developed and scanned. The blots were then stripped and re-probed with an anti-beta tubulin antibody (Sigma) as a control. After densitometric analysis, the E7 protein levels were normalised against the beta-tubulin levels.

Figure 6:
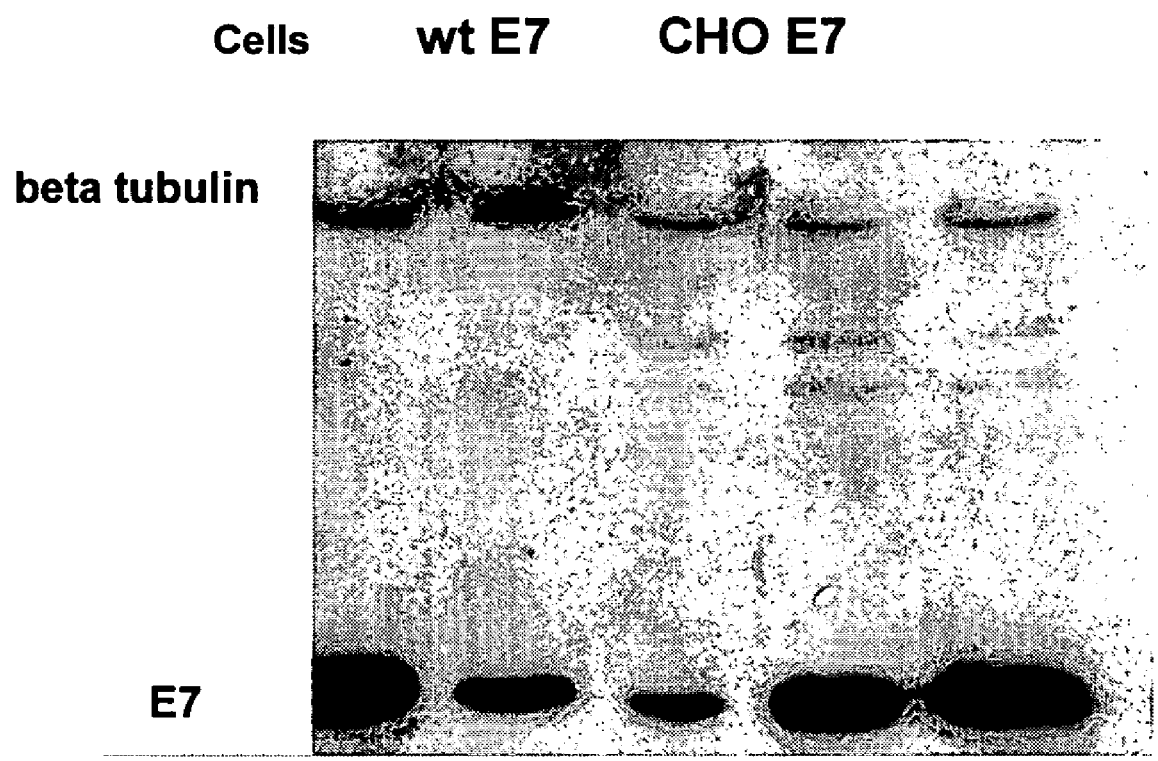
FIG. 6 is a photographic representation of a western blot showing that the production of HPV16E7 in CHO cells is about 2.5 times higher from the codon-modified HPV16E7 nucleotide sequence [SEQ ID NO:6] than from the parent or unmodified HPV16E7 nucleotide sequence [SEQ ID NO:4].

The results presented in FIG. 6 show that the codon modified HPV16E7 construct produces about 2.5 times more HPV16E7 than the unmodified HPV16E7 construct.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method of constructing a synthetic polynucleotide from which a polypeptide is producible at a higher level in a Chinese Hamster Ovary (CHO) cell than from a parent polynucleotide encoding the same polypeptide, the method comprising:
   selecting a first codon of the parent polynucleotide for replacement with a synonymous codon, wherein the synonymous codon is selected on the basis that it exhibits a higher translational efficiency in the CHO cell than the first codon in a comparison of translational efficiencies of codons in test CHO cells; and
   replacing the first codon with the synonymous codon to construct the synthetic polynucleotide,
wherein the first and synonymous codons are selected from the following Table:

| First Codon | Synonymous Codon |
|---|---|
| Ala$^{GCC}$ | Ala$^{GCA}$ |
| Ala$^{GCC}$ | Ala$^{GCG}$ |
| Ala$^{GCC}$ | Ala$^{GCT}$ |
| Ala$^{GCT}$ | Ala$^{GCA}$ |
| Ala$^{GCG}$ | Ala$^{GCA}$ |
| Arg$^{CGC}$ | Arg$^{AGA}$ |
| Arg$^{CGC}$ | Arg$^{CGA}$ |
| Arg$^{CGC}$ | Arg$^{CGG}$ |
| Arg$^{CGC}$ | Arg$^{CGT}$ |
| Arg$^{CGC}$ | Arg$^{AGG}$ |
| Asp$^{GAC}$ | Asp$^{GAT}$ |
| Glu$^{GAG}$ | Glu$^{GAA}$ |
| Gly$^{GGT}$ | Gly$^{GGA}$ |
| Gly$^{GGC}$ | Gly$^{GGA}$ |
| Gly$^{GGC}$ | Gly$^{GGG}$ |
| Gly$^{GGG}$ | Gly$^{GGA}$ |
| Leu$^{CTT}$ | Leu$^{TTG}$ |
| Leu$^{CTG}$ | Leu$^{CTC}$ |
| Leu$^{CTG}$ | Leu$^{TTG}$ |
| Leu$^{CTA}$ | Leu$^{TTG}$ |
| Leu$^{CTT}$ | Leu$^{CTA}$ |
| Leu$^{TTA}$ | Leu$^{CTA}$ |
| Phe$^{TTC}$ | Phe$^{TTT}$ |
| Thr$^{ACC}$ | Thr$^{ACT}$ |
| Thr$^{ACC}$ | Thr$^{ACG}$ |
| Thr$^{ACC}$ | Thr$^{ACA}$ |

2. A method according to claim 1, wherein the polypeptide is selected from the group consisting of etanercept, HPV16E7 and human growth hormone.

3. A method of producing a polypeptide in a Chinese Hamster Ovary (CHO) cell from a synthetic polynucleotide at a higher level than from a parent polynucleotide encoding the same polypeptide, the method comprising:
   selecting a first codon of the parent polynucleotide for replacement with a synonymous codon, wherein the synonymous codon is selected on the basis that it exhibits a higher translational efficiency in the CHO cell than the first codon in a comparison of translational efficiencies of codons in test CHO cells, wherein both the first and synonymous codons are selected from the following Table:

| First Codon | Synonymous Codon |
|---|---|
| Ala$^{GCC}$ | Ala$^{GCA}$ |
| Ala$^{GCC}$ | Ala$^{GCG}$ |
| Ala$^{GCC}$ | Ala$^{GCT}$ |
| Ala$^{GCT}$ | Ala$^{GCA}$ |
| Ala$^{GCG}$ | Ala$^{GCA}$ |
| Arg$^{CGC}$ | Arg$^{AGA}$ |
| Arg$^{CGC}$ | Arg$^{CGA}$ |
| Arg$^{CGC}$ | Arg$^{CGG}$ |
| Arg$^{CGC}$ | Arg$^{CGT}$ |
| Arg$^{CGC}$ | Arg$^{AGG}$ |
| Asp$^{GAC}$ | Asp$^{GAT}$ |
| Glu$^{GAG}$ | Glu$^{GAA}$ |
| Gly$^{GGT}$ | Gly$^{GGA}$ |
| Gly$^{GGC}$ | Gly$^{GGA}$ |
| Gly$^{GGC}$ | Gly$^{GGG}$ |
| Gly$^{GGG}$ | Gly$^{GGA}$ |
| Leu$^{CTT}$ | Leu$^{TTG}$ |
| Leu$^{CTG}$ | Leu$^{CTC}$ |
| Leu$^{CTG}$ | Leu$^{TTG}$ |
| Leu$^{CTA}$ | Leu$^{TTG}$ |
| Leu$^{CTT}$ | Leu$^{CTA}$ |
| Leu$^{TTA}$ | Leu$^{CTA}$ |
| Phe$^{TTC}$ | Phe$^{TTT}$ |
| Thr$^{ACC}$ | Thr$^{ACT}$ |
| Thr$^{ACC}$ | Thr$^{ACG}$ |
| Thr$^{ACC}$ | Thr$^{ACA}$ | replacing the first codon with the synonymous codon to construct the synthetic polynucleotide;
   introducing the synthetic polynucleotide into the CHO cell; and
   expressing the synthetic polynucleotide in the CHO cell, whereby the polypeptide is produced from the synthetic polynucleotide in the CHO cell at a higher level than from the parent polynucleotide.

4. A method according to claim 3, further comprising isolating or purifying the polypeptide from the CHO cell.

5. A method of producing a virus particle in a Chinese Hamster Ovary (CHO) cell, wherein the virus particle comprises a polypeptide necessary for assembly of the virus particle, and wherein the polypeptide is produced in the CHO cell from a parent polynucleotide, but not at a level sufficient to permit productive virus assembly therein, the method comprising:
   selecting a first codon of the parent polynucleotide for replacement with a synonymous codon, wherein the synonymous codon is selected on the basis that it exhibits a higher translational efficiency in the CHO cell than the first codon in a comparison of translational efficiencies of codons in test CHO cells, wherein both the first and synonymous codons are selected from the following Table:

| First Codon | Synonymous Codon |
|---|---|
| $Ala^{GCC}$ | $Ala^{GCA}$ |
| $Ala^{GCC}$ | $Ala^{GCG}$ |
| $Ala^{GCC}$ | $Ala^{GCT}$ |
| $Ala^{GCT}$ | $Ala^{GCA}$ |
| $Ala^{GCG}$ | $Ala^{GCA}$ |
| $Arg^{CGC}$ | $Arg^{AGA}$ |
| $Arg^{CGC}$ | $Arg^{CGA}$ |
| $Arg^{CGC}$ | $Arg^{CGG}$ |
| $Arg^{CGC}$ | $Arg^{CGT}$ |
| $Arg^{CGC}$ | $Arg^{AGG}$ |
| $Asp^{GAC}$ | $Asp^{GAT}$ |
| $Glu^{GAG}$ | $Glu^{GAA}$ |
| $Gly^{GGT}$ | $Gly^{GGA}$ |
| $Gly^{GGC}$ | $Gly^{GGA}$ |
| $Gly^{GGC}$ | $Gly^{GGG}$ |
| $Gly^{GGG}$ | $Gly^{GGA}$ |

-continued

| First Codon | Synonymous Codon |
|---|---|
| $Leu^{CTT}$ | $Leu^{TTG}$ |
| $Leu^{CTG}$ | $Leu^{CTC}$ |
| $Leu^{CTG}$ | $Leu^{TTG}$ |
| $Leu^{CTA}$ | $Leu^{TTG}$ |
| $Leu^{CTT}$ | $Leu^{CTA}$ |
| $Leu^{TTA}$ | $Leu^{CTA}$ |
| $Phe^{TTC}$ | $Phe^{TTT}$ |
| $Thr^{ACC}$ | $Thr^{ACT}$ |
| $Thr^{ACC}$ | $Thr^{ACG}$ |
| $Thr^{ACC}$ | $Thr^{ACA}$ | replacing the first codon with the synonymous codon to construct the synthetic polynucleotide; and
introducing into the CHO cell the synthetic polynucleotide operably linked to a regulatory polynucleotide,
whereby the synthetic polynucleotide is expressed to produce the polypeptide at a level sufficient to permit the production of the virus particle in the CHO cell.

6. A method according to claim 5, further comprising isolating or purifying the virus particle from the CHO cell.

* * * * *